(12) United States Patent
Kotanko et al.

(10) Patent No.: US 12,046,375 B2
(45) Date of Patent: Jul. 23, 2024

(54) SYSTEM AND METHOD FOR ATTAINING DESIRED OXYGEN DOSING BASED ON ERYTHROPOIESIS MODELING

(71) Applicants: Fresenius Medical Care Holdings, Inc., Waltham, MA (US); Fresenius Medical Care Deutschland GmbH, Bad Homburg (DE)

(72) Inventors: Peter Kotanko, New York, NY (US); Ulrike Kotanko, Waltham, MA (US); Sabrina Casper, Bad Homburg (DE); David Joerg, Bad Homburg (DE); Gudrun Schappacher-Tilp, Waltham, MA (US); Doris Fuertinger, Long Island City, NY (US)

(73) Assignees: Fresenius Medical Care Holdings, Inc., Waltham, MA (US); Fresenius Medical Care Deutschland GmbH, Bad Homburg (DE)

( * ) Notice: Subject to any disclaimer, the term of this patent is extended or adjusted under 35 U.S.C. 154(b) by 141 days.

(21) Appl. No.: 17/960,560

(22) Filed: Oct. 5, 2022

(65) Prior Publication Data

US 2024/0127962 A1   Apr. 18, 2024

(51) Int. Cl.
*G16H 50/50* (2018.01)
*G16H 50/30* (2018.01)

(52) U.S. Cl.
CPC .............. *G16H 50/50* (2018.01); *G16H 50/30* (2018.01)

(58) Field of Classification Search
CPC ........ G16H 50/50; G16H 50/30; G16H 20/30; G16H 40/67; G16H 50/20; A61B 5/7267;
(Continued)

(56) References Cited

U.S. PATENT DOCUMENTS 6,054,427 A * 4/2000 Winslow ................... A61P 7/08
514/832
9,679,111 B2   6/2017 Fuertinger et al.
(Continued)

FOREIGN PATENT DOCUMENTS

WO   WO 2013/036836 A2   3/2013
WO   WO 2016/100875 A2   6/2016

OTHER PUBLICATIONS

Besarab et al., *J. Am. Soc. Nephrol.*, 27(4), 1225-1233 (Apr. 2016).
(Continued)

*Primary Examiner* — Eliza A Lam
(74) *Attorney, Agent, or Firm* — Leydig, Voit & Mayer, Ltd.

(57) ABSTRACT

A computing system for determining a systematic training strategy for the user is provided. The computing system includes a user device that uses one or more sensors to obtain partial pressure of oxygen (PO2) levels of a user over a period of time. The user device provides previous PO2 levels to a personalized erythropoiesis model generation computing platform. The computing platform obtains individualized user data for the user indicating or more previous hematocrit and/or hemoglobin measurements for the user. The computing platform determines an individualized erythropoiesis model for the user based on the one or more previous hematocrit and/or hemoglobin measurements and the previous PO2 information, and employs the individualized erythropoiesis model to determine predicted hematocrit and/or hemoglobin measurements. The computing platform performs one or more actions based on the one or more predicted hematocrit and/or hemoglobin measurements.

20 Claims, 18 Drawing Sheets

(58) Field of Classification Search
CPC .............. A61B 5/7282; A61B 5/7239; A61B 2505/09; A61B 5/4842; A61B 5/14535
See application file for complete search history.

(56) References Cited

U.S. PATENT DOCUMENTS

| | | |
|---|---|---|
| 9,801,993 B2 | 10/2017 | Barrett et al. |
| 10,319,478 B2* | 6/2019 | Fuertinger ............ G16H 50/50 |
| 2014/0128791 A1 | 5/2014 | Fuertinger et al. |
| 2016/0180053 A1 | 6/2016 | Fuertinger et al. |
| 2019/0019570 A1 | 1/2019 | Fuertinger et al. |
| 2021/0272696 A1* | 9/2021 | DeMazumder ........ G16H 15/00 |

OTHER PUBLICATIONS

Fuertinger et al., *J. Math. Biol.*, 66, 1209-1240 (2013).
Fuertinger et al., *CPT Pharmacometrics Syst. Pharmacol.* 7, 219-227, (2018).
Fuertinger et al., *PLOS-ONE*, e0195918 (Apr. 18, 2018).
Heinicke et al. *Eur. J. Appl. Physiol.*, 88, 535-543 (2003).
Nangaku et al., *Nephrol. Dial. Transplant*, 36, 1731-1741 (2021).
Chapman et al., *J. Science and Medicine in Sport*, 13(6), 624-629 (2010).
Flaherty et al., *Travel Med. and Infectious Disease*, 14(3), 200-211 (2016).
Gunga et al., *Respiratory Physiology and Neurobiology*, 158(2-3), 287-297 (2007).
International Patent Application No. PCT/US2023/032953, Search Report (Dec. 7, 2023).

* cited by examiner

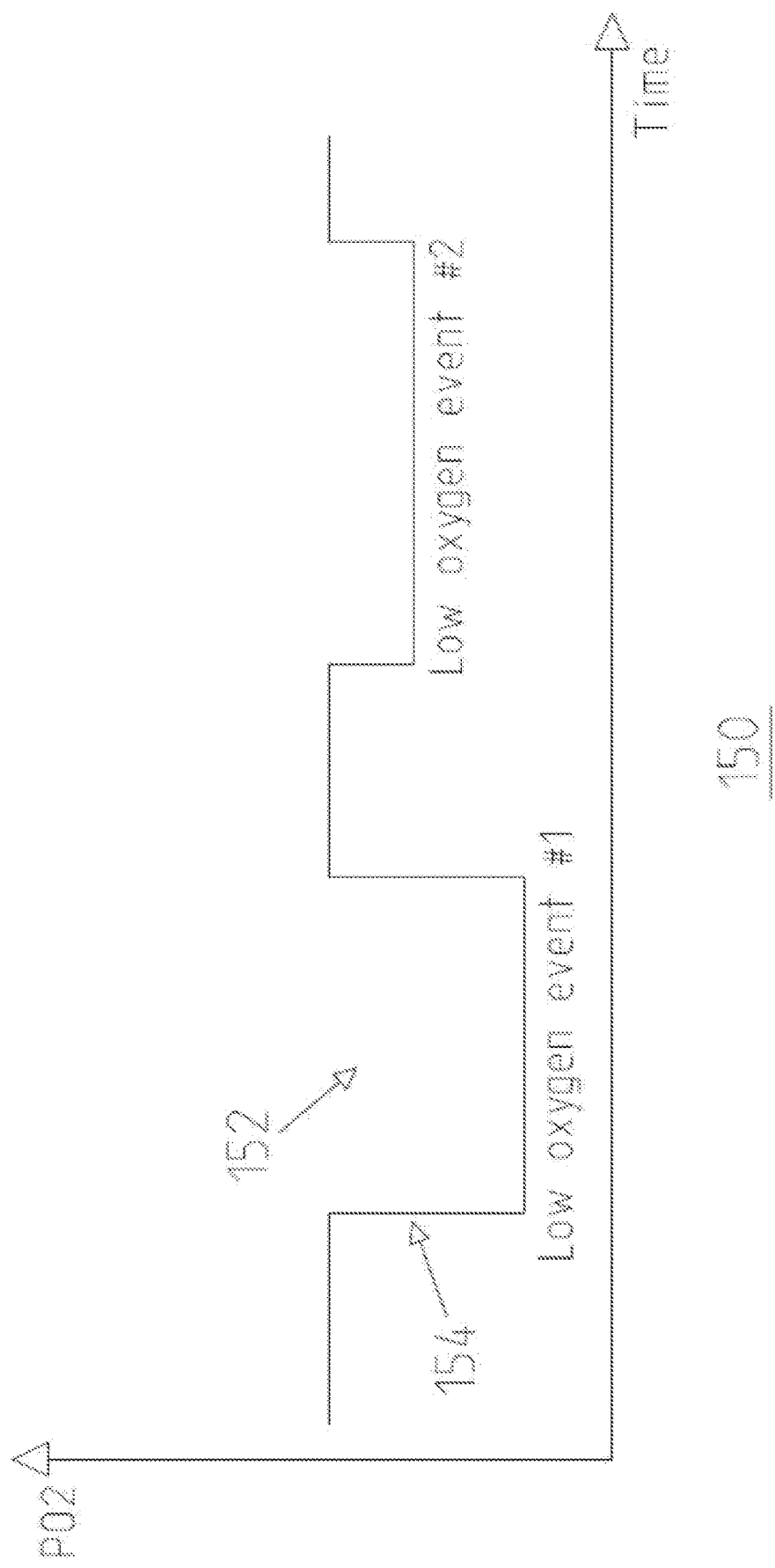

SYSTEM AND METHOD FOR ATTAINING DESIRED OXYGEN DOSING BASED ON ERYTHROPOIESIS MODELING

BACKGROUND

Red blood cells (erythrocytes) are essential for the transport of oxygen through the body. An understanding of the regulation of red blood cell production, called erythropoiesis, is important for the treatment of patients in a variety of clinical situations as well as other users such as athletes. For instance, athletes may seek to achieve a desired hemoglobin level and/or oxygen dosing level prior to a particular event such as a sports competition. By achieving the desired hemoglobin level, athletes may perform to their peek potential. In other example, patients with planned surgeries would seek to achieve a certain hemoglobin level prior to the surgery in order to reduce the risk of the surgery. As such, users may take precautions and/or perform actions to reach the desired hemoglobin level such as training at high altitudes, within low oxygen chambers, and/or take other measures. However, it is difficult for users to accurately predict what their desired hemoglobin level and/or oxygen dosing level would be at a particular time in the future (e.g., at the particular event such as a planned surgery or sports event).

SUMMARY

This summary is provided to introduce certain exemplary embodiments that are further described below. This summary is not intended to be an identification of key features or essential features of the present disclosure.

In an embodiment, a computing system is provided. The computing system comprises a user device, comprising: one or more sensors configured to obtain partial pressure of oxygen (PO2) levels; one or more first processors; and a first non-transitory computer-readable medium having first processor-executable instructions stored thereon, wherein the first processor-executable instructions, when executed by the one or more first processors, facilitate: obtaining, using the one or more sensors, the PO2 levels over a period of time; generating previous PO2 information for a user based on the PO2 levels obtained using the one or more sensors; and providing the previous PO2 information to a personalized erythropoiesis model generation computing platform; and the personalized erythropoiesis model generation computing platform, comprising: one or more second processors; and a second non-transitory computer-readable medium having second processor-executable instructions stored thereon, wherein the second processor-executable instructions, when executed by the one or more second processors, facilitate: obtaining the previous PO2 information from the user device; obtaining individualized user data for the user, wherein the individualized user data indicates one or more previous hematocrit and/or hemoglobin measurements for the user; determining an individualized erythropoiesis model for the user based on the one or more previous hematocrit and/or hemoglobin measurements and the previous PO2 information, wherein the individualized erythropoiesis model indicates a set of individualized model parameters for the user; employing the individualized erythropoiesis model to determine one or more predicted hematocrit and/or hemoglobin measurements at one or more future instances in time; and performing one or more actions based on the one or more predicted hematocrit and/or hemoglobin measurements.

In some instances, determining the individualized erythropoiesis model for the user comprises: inputting the previous PO2 information and the one or more previous hematocrit and/or hemoglobin measurements into a mathematical model for oxygen dosing to determine the individualized erythropoiesis model.

In some examples, the previous PO2 information indicates one or more low oxygen events experienced by the user over a previous time period, wherein each of the one or more low oxygen events indicates a PO2 level that is below a normoxia level.

In some variations, employing the individualized erythropoiesis model to determine the one or more predicted hematocrit and/or hemoglobin measurements comprises: generating a plurality of future PO2 information, wherein each of the plurality of future PO2 information indicates one or more low oxygen events for the user to perform in a future time period; inputting the plurality of future PO2 information into the individualized erythropoiesis model to determine a plurality of predicted hematocrit and/or hemoglobin measurements; and determining an optimal future PO2 information from the plurality of future PO2 information based on comparing the plurality of predicted hematocrit and/or hemoglobin measurements with a desired hematocrit and/or hemoglobin measurement associated with the user.

In some instances, the second processor-executable instructions, when executed by the one or more second processors, further facilitate: determining a systematic training strategy for the user based on the optimal future PO2 information, and wherein performing the one or more actions comprises displaying the systematic training strategy on a display device associated with the personalized erythropoiesis model generation computing platform.

In some examples, the first processor-executable instructions, when executed by the one or more first processors, further facilitate: generating additional PO2 information for the user based on the PO2 levels obtained using the one or more sensors; and providing the additional PO2 information to the personalized erythropoiesis model generation computing platform.

In some variations, wherein the second processor-executable instructions, when executed by the one or more second processors, further facilitate: subsequent to employing the individualized erythropoiesis model, determining whether to re-employ the individualized erythropoiesis model; and re-employing the individualized erythropoiesis model using the additional PO2 information from the user device.

In some instances, the first processor-executable instructions, when executed by the one or more first processors, further facilitate: obtaining a mathematical model for oxygen dosing; obtaining population user data associated with a plurality of users; and generating a plurality of virtual user avatars based on the mathematical model and the population user data, wherein determining the individualized erythropoiesis model for the user is further based on the plurality of virtual user avatars.

In some examples, determining the individualized erythropoiesis model for the user is based on the following equation:

$$\frac{dh}{dt} = \beta_h(\theta)\varphi_{a_h,b_h,q_{h,0}}(k_h[\sigma_{O_2} - \sigma^*_{O_2}]) - k_h h, \text{ where } \frac{dh}{dt}$$

indicates a rate of change of hypoxia-inducible factor (HIF) signaling activity, $\beta_h(\theta)$ indicates a formation rate of HIF complexes, $\varphi_{a_h,b_h,q_{h,0}}$ indicates a hypoxic upregulation of a HIF signal in response to decreases in blood hemoglobin concentration, $k_h$ indicates a decay rate of the HIF signal, $\sigma_{O_2}$ indicates a blood hemoglobin concentration measured by kidneys, $\sigma_{O_2}^*$ indicates a physiological set point for the concentration of oxygenated hemoglobin in blood, and h indicates the HIF signal.

In some variations, determining the individualized erythropoiesis model for the user is based on the following equation:

$$\frac{de}{dt} = \beta_e(\theta) + \beta_e(\theta)\varphi_{a_e,b_e,q_{e,0}}(k_e h) - k_e e, \text{ where } \frac{de}{dt}$$

indicates a EPO concentration rate of change, $\beta_e(\theta)$ indicates basal erythropoietin (EPO) synthesis under steady-state conditions, $\beta_e(\theta)\varphi_{a_e,b_e,q_{e,0}}(k_e h)$ indicates additional EPO synthesis due to activation by a HIF signal, and $k_e e$ indicates EPO decay with a decay rate $k_e$.

In some instances, determining the individualized erythropoiesis model for the user is based on the following equation:

$$\frac{dn_{ery}}{dt} = 2^{d_{pre}} J_{pre \to ery} - K_{ery}, \text{ where } \frac{dn_{ery}}{dt}$$

indicates a rate of change of the total amount of red blood cells, $2^{d_{pre}} J_{pre \to ery}$ indicates a differentiation flux from a precursors population to an erythrocytes population, and $K_{ery}$ indicates cell fluxes due to apoptosis.

In another embodiment, a method is provided. The method comprises: obtaining individualized user data for a user, wherein the individualized user data indicates one or more previous hematocrit and/or hemoglobin measurements for the user and previous partial pressure of oxygen (PO2) information for the user; determining an individualized erythropoiesis model for the user based on the one or more previous hematocrit and/or hemoglobin measurements and the previous PO2 information, wherein the individualized erythropoiesis model indicates a set of individualized model parameters for the user; employing the individualized erythropoiesis model to determine one or more predicted hematocrit and/or hemoglobin measurements at one or more future instances in time; and performing one or more actions based on the one or more predicted hematocrit and/or hemoglobin measurements.

In some instances, determining the individualized erythropoiesis model for the user comprises: inputting the previous PO2 information and the one or more previous hematocrit and/or hemoglobin measurements into a mathematical model for oxygen dosing to determine the individualized erythropoiesis model.

In some examples, the previous PO2 information indicates one or more low oxygen events experienced by the user over a previous time period, wherein each of the one or more low oxygen events indicates a PO2 level that is below a normoxia level.

In some variations, employing the individualized erythropoiesis model to determine the one or more predicted hematocrit and/or hemoglobin measurements comprises: generating a plurality of future PO2 information, wherein each of the plurality of future PO2 information indicates one or more low oxygen events for the user to perform in a future time period; inputting the plurality of future PO2 information into the individualized erythropoiesis model to determine a plurality of predicted hematocrit and/or hemoglobin measurements; and determining an optimal future PO2 information from the plurality of future PO2 information based on comparing the plurality of predicted hematocrit and/or hemoglobin measurements with a desired hematocrit and/or hemoglobin measurement associated with the user.

In some instances, the method further comprises: determining a systematic training strategy for the user based on the optimal future PO2 information, and wherein performing the one or more actions comprises displaying the systematic training strategy on a display device associated with the personalized erythropoiesis model generation computing platform.

In some examples, determining the individualized erythropoiesis model for the user is based on the following equation:

$$\frac{dh}{dt} = \beta_h(\theta)\varphi_{a_h,b_h,q_{h,0}}(k_h[\sigma_{O_2} - \sigma_{O_2}^*]) - k_h h, \text{ where } \frac{dh}{dt}$$

indicates a rate of change of hypoxia-inducible factor (HIF) signaling activity, $\beta_h(\theta)$ indicates a formation rate of HIF complexes, $\varphi_{a_h,b_h,q_{h,0}}$ indicates a hypoxic upregulation of a HIF signal in response to decreases in blood hemoglobin concentration, $k_h$ indicates a decay rate of the HIF signal, $\sigma_{O_2}$ indicates a blood hemoglobin concentration measured by kidneys, $\sigma_{O_2}^*$ indicates a physiological set point for the concentration of oxygenated hemoglobin in blood, and h indicates the HIF signal.

In some variations, determining the individualized erythropoiesis model for the user is based on the following equation:

$$\frac{de}{dt} = \beta_e(\theta) + \beta_e(\theta)\varphi_{a_e,b_e,q_{e,0}}(k_e h) - k_e e, \text{ where } \frac{de}{dt}$$

indicates a EPO concentration rate of change, $\beta_e(\theta)$ indicates basal erythropoietin (EPO) synthesis under steady-state conditions, $\beta_e(\theta)\varphi_{a_e,b_e,q_{e,0}}(k_e h)$ indicates additional EPO synthesis due to activation by a HIF signal, and $k_e e$ indicates EPO decay with a decay rate $k_e$.

In some instances, determining the individualized erythropoiesis model for the user is based on the following equation:

$$\frac{dn_{ery}}{dt} = 2^{d_{pre}} J_{pre \to ery} - K_{ery}, \text{ where } \frac{dn_{ery}}{dt}$$

indicates a rate of change of the total amount of red blood cells, $2^{d_{pre}} J_{pre \to ery}$ indicates a differentiation flux from a precursors population to an erythrocytes population, and $K_{ery}$ indicates cell fluxes due to apoptosis.

In yet another embodiment, a personalized erythropoiesis model generation computing platform is provided. The computing platform comprises: one or more processors; and a non-transitory computer-readable medium having processor-executable instructions stored thereon, wherein the processor-executable instructions, when executed by the one or more processors, facilitate: obtaining individualized user data for a user, wherein the individualized user data indicates one or more previous hematocrit and/or hemoglobin measurements for the user and previous partial pressure of oxygen (PO2) information for the user; determining an individualized erythropoiesis model for the user based on the one or more previous hematocrit and/or hemoglobin measurements and the previous PO2 information, wherein the individualized erythropoiesis model indicates a set of individualized model parameters for the user; employing the individualized erythropoiesis model to determine one or more predicted hematocrit and/or hemoglobin measurements at one or more future instances in time; and performing one or more actions based on the one or more predicted hematocrit and/or hemoglobin measurements.

Further features and aspects are described in additional detail below with reference to the figures.

BRIEF DESCRIPTION OF THE DRAWINGS

FIG. 1B is a graphical representation of partial pressure of oxygen (PO2) information in accordance with one or more examples of the present application.

DETAILED DESCRIPTION

Figure 1A:
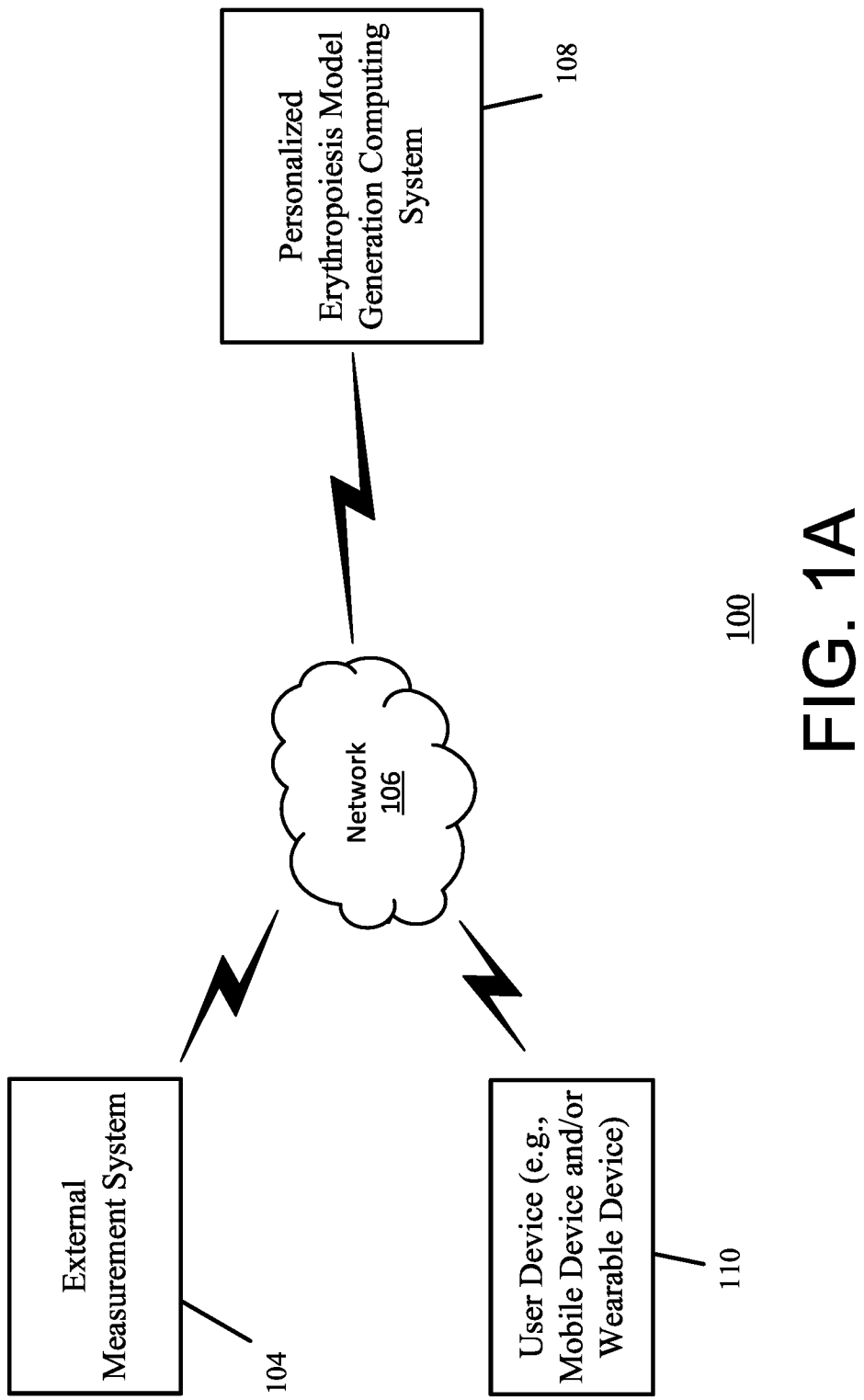
FIG. 1A is a simplified block diagram depicting an exemplary computing environment in accordance with one or more examples of the present application.

Exemplary embodiments of the present application provide for generating erythropoiesis models for one or more users and using the erythropoiesis models to adjust the users' hematocrit and/or hemoglobin concentrations. Examples of modeling erythropoiesis (including using iron homeostasis) with a selected erythropoiesis stimulating agent (ESA) administration regimen, predicting a patient's hematocrit and/or hemoglobin (HGB) concentration with the initially selected ESA administration regimen, employing the model to determine one or more different ESA administration regimens such that the model predicts the patient's hematocrit and/or hemoglobin concentrations are within the desired range, and administering the ESA to the patient with the determined ESA administration regimen are described in U.S. Pat. No. 10,319,478, titled "SYSTEM AND METHOD OF MODELING ERYTHROPOIESIS AND ITS MANAGEMENT," and U.S. Pat. No. 9,679,111, titled "SYSTEM AND METHOD OF MODELING ERYTHROPOIESIS INCLUDING IRON HOMEOSTASIS", which are incorporated by reference in their entirety herein. Also incorporated herein by reference in its entirety is U.S. patent application Ser. No. 17/960,305, titled "SYSTEM AND METHOD FOR ADJUSTING HYPDXIA-INDUCIBLE FACTOR STABILIZER TREATMENT BASED ON ANEMIA MODELING", filed on Oct. 5, 2022.

As will be explained in further detail below, the present disclosure describes systems, devices, and methods for generating and using erythropoiesis models. For instance, the new erythropoiesis model enables prediction of an individual's HGB dynamics as a function of EPO levels and other user-specific characteristics. These user specific characteristics may be identified following systematic perturbations to the user (e.g., periods of low oxygen). Exposure of the user to lower air pressure, e.g., at high altitudes, leads to lower inspiratory O2 partial pressure, PO2. Likewise, exposure of the user to an atmosphere with a reduced ambient fractional oxygen (O2) concentration also leads to a lower inspiratory PO2. This lower inspiratory PO2 results in hypoxemia, a potent physiological stimulus of EPO synthesis. Measurements of HGB and EPO levels before, during and after the PO2 perturbation allows for the identification of key biological parameters of the new erythropoiesis model, resulting in a user-specific avatar. The avatar may be used to predict the user's temporal, quantitative HGB response to intermittent PO2 reductions.

Among other advantages, the present disclosure uses erythropoiesis models to accurately predict desired hemoglobin and/or oxygen dosing level at a future time. For instance, because every user is different, the erythropoiesis models are used to better predict a specific individual's reaction to certain events and how those events would impact the individual's hemoglobin and/or oxygen dosing levels, which in turn is capable of more accurately predicting or determining hemoglobin and/or oxygen dosing levels at a future instance in time. For example, hemoglobin is the principle means to carry oxygen from the lungs to the peripheral organs and tissues. While low HGB levels result in fatigue and physical weakness, higher-than-normal HGB levels (up to a point) result in improved physical performance and stamina. These characteristics are desirable in some users, particularly those who are expected to benefit from a higher hematocrit at a given point in time (e.g., athletes prior to sport events, Special Forces, and/or high endurance endeavors). In addition, these characteristics are desirable in situations where substantial blood loss is expected (e.g., future major surgery), in situations where blood donations are preferred (e.g., in preparation of surgery with expected high blood loss), in users who cannot be given ESAs because of pre-existing conditions (e.g., vascular access occlusion, history of seizures, allergic reactions to ESA, hypertension, and/or hyper coagulopathies), and/or in users who prefer not to receive this class of drugs and instead prefer physiological over pharmacological means to increase red blood cell mass.

FIG. 1A is a simplified block diagram depicting an exemplary computing environment (e.g., computing system) in accordance with one or more examples of the present application. The environment 100 includes an external measurement system 104, a network 106, a personalized erythropoiesis model generation computing system 108 (e.g., personalized erythropoiesis model generation computing platform), and a user device 110 (e.g., a mobile device and/or a wearable device). Although the entities within environment 100 may be described below and/or depicted in the FIGs. as being singular entities, it will be appreciated that the entities and functionalities discussed herein may be implemented by and/or include one or more entities.

The entities within the environment 100 such as the external measurement system 104, the personalized erythropoiesis model generation computing system 108, and the user device 110 may be in communication with other systems within the environment 100 via the network 106. The network 106 may be a global area network (GAN) such as the Internet, a wide area network (WAN), a local area network (LAN), or any other type of network or combination of networks. The network 106 may provide a wireline, wireless, or a combination of wireline and wireless communication between the entities within the environment 100. Additionally, and/or alternatively, one or more entities within the environment 100 may be in communication with each other without using the network 106. For instance, the external measurement computing device 104 and the user device 110 may be in communication with each other via one or more wireless protocols (e.g., WI-FI) and/or wired connections.

The user device 110 may be a mobile phone such as a smartphone that is owned and/or operated by a user and/or a wearable device. The user may provide information to the other entities of environment 100 such as the personalized erythropoiesis model generation computing system 108 using the user device 110, and the user device 110 may receive information from the other entities. For example, the user device 110 may receive user input from the user such as hemoglobin or hematocrit concentrations of the user, event information such as low oxygen events (e.g., intense training events, high altitude events, low oxygen chamber events, high endurance events, and/or other events to prepare for a performance event) and performance events (e.g., a future surgery, athletic competitions, blood donations, other medical events, and/or other types of performance events), and/or a future time for the event information (e.g., a date when the performance event is scheduled to occur). The low oxygen events may include and/or indicate PO2 information of the user. The PO2 information may refer to ambient and/or inspiratory, depending on the situation. For example, for high altitude training the ambient PO2 may be suitable, whereas the inspiratory PO2 may be more suitable when ambient PO2 is normal and the low PO2 event is a result of utilizing a high-altitude training mask. FIG. 1B is a graphical representation of reduced oxygen partial pressure (PO2) information in accordance with one or more examples of the present application. In particular, FIG. 1B shows a graphical representation 150 of a time series of PO2 levels of a user (e.g., PO2 levels of the user over a set period of time). For instance, the graphical representation 150 includes a normoxia level 152 (e.g., a normal level of oxygen for the user) and observed PO2 levels of the user 154. The observed PO2 levels of the user 154 decrease below the normoxia level 152 at two different instances. Each of these two instances may indicate a low oxygen event (e.g., "Low oxygen event #1" and "Low oxygen event #2"). As such, the PO2 information may indicate one or more low oxygen events over a period of time such as the example shown by graphical representation 150. In some variations, the user may provide user input indicating the low oxygen events (e.g., PO2 levels over a period of time), and the user device 110 may generate the PO2 information based on the user input.

Additionally, and/or alternatively, in some examples, the user device 110 may include one or more sensors and/or other devices configured to obtain the low oxygen events and/or generate the PO2 information. For instance, the user device 110 may be a wearable device that includes one or more sensors configured to obtain oxygen saturation and/or partial pressure of the user's surroundings. Based on the obtained sensor data, the user device 110 may generate the PO2 information. For example, the user device 110 may be a wearable device that is worn by the user and/or a mobile device. The user device 110 may continuously measure PO2 levels of the environment surrounding the user, and generate the PO2 information based on the continuous measurements.

Additionally, and/or alternatively, the user device 110 may receive information from other entities of the environment 100 such as from the personalized erythropoiesis model generation computing system 108. For instance, the personalized erythropoiesis model generation computing system 108 may generate and provide oxygen dosing information to the user device 110. In some instances, the oxygen dosing information may indicate a user's measured hemoglobin or hematocrit concentration and/or a predicted hemoglobin or hematocrit concentration at a future instance in time (e.g., when the performance event is scheduled to occur). Additionally, and/or alternatively, the oxygen dosing information may indicate one or more low oxygen events for the user to perform so as to obtain the desired hemoglobin or hematocrit levels at the future time for when the performance event is scheduled to occur.

In some variations, the oxygen dosing information may include an erythropoiesis model for the user. For instance, the oxygen dosing information may include a generic erythropoiesis model (e.g., an erythropoiesis model that is not specific to the individual). The user device 110 may be configured to individualize the erythropoiesis model for the user, with individualized model parameters that are specific to the user, prior to using the individualized erythropoiesis model to predict hemoglobin or hematocrit levels for the user. Additionally, and/or alternatively, the oxygen dosing information may include an individualized erythropoiesis model with individualized model parameters that are specific to the user. The generation of the generic or individualized erythropoiesis model for the user as well as the use of the erythropoiesis model to predict hematocrit and/or hemoglobin levels for the user will be described in further detail below.

The user device 110 may be and/or include, but is not limited to, a desktop, laptop, tablet, mobile device (e.g., smartphone device, or other mobile device), smart watch, an internet of things (IOT) device, wearable device, or any other type of computing device that generally comprises one or more communication components, one or more processing components, and one or more memory components. The user device 110 may be able to execute software applications managed by, in communication with, and/or otherwise associated with an enterprise organization.

The personalized erythropoiesis model generation computing system 108 is a computing system that generates one or more personalized erythropoiesis models. For example, the personalized erythropoiesis model generation computing system 108 includes one or more computing devices, computing platforms, systems, servers, and/or other apparatuses capable of performing functions and/or actions such as generating one or more personalized erythropoiesis models for a user.

In some instances, the personalized erythropoiesis model generation computing system 108 may, for example, communicate with the external measurement system 104 and/or the user device 110. For instance, the personalized erythropoiesis model generation computing system 108 may provide the one or more generated personalized erythropoiesis to the user device 110. In some examples, the personalized erythropoiesis model generation computing system 108 may include a display device that is configured to display information associated with the erythropoiesis model.

The personalized erythropoiesis model generation computing system 108 may be implemented using one or more computing platforms, devices, servers, and/or apparatuses. In some examples, the computing system 108 may include and/or be connected to a display device that is configured to display information. In some variations, the personalized erythropoiesis model generation computing system 108 may be implemented as engines, software functions, and/or applications. In other words, the functionalities of the personalized erythropoiesis model generation computing system 108 may be implemented as software instructions stored in storage (e.g., memory) and executed by one or more processors.

The external measurement system 104 may be and/or include, but is not limited to, one or more desktops, laptops, tablets, mobile devices (e.g., smartphone device, or other mobile device), processors, controllers, or any other type of computing device that generally comprises one or more communication components, one or more processing components, and one or more memory components.

The external measurement system 104 may be configured to measure and/or obtain measurements associated with the user. For instance, the external measurement system 104 may be a lab system that is configured to measure hemoglobin or hematocrit levels and/or erythropoietin levels of the user based on a blood sample of the user. After obtaining the measured hemoglobin or hematocrit levels and/or the erythropoietin levels, the external measurement system 104 may be configured to provide measured hemoglobin or hematocrit levels to other entities within environment 100.

In some instances, a singular entity may perform the functionalities of the user device 110 and the personalized erythropoiesis model generation computing system 108. For instance, the personalized erythropoiesis computing system 108 may generate the personalized erythropoiesis models and use the personalized erythropoiesis models to predict a user's hematocrit and/or hemoglobin levels at a future instance in time.

It will be appreciated that the exemplary environment depicted in FIG. 1A is merely an example, and that the principles discussed herein may also be applicable to other situations—for example, including other types of institutions, organizations, devices, systems, and network configurations.

Figure 2:
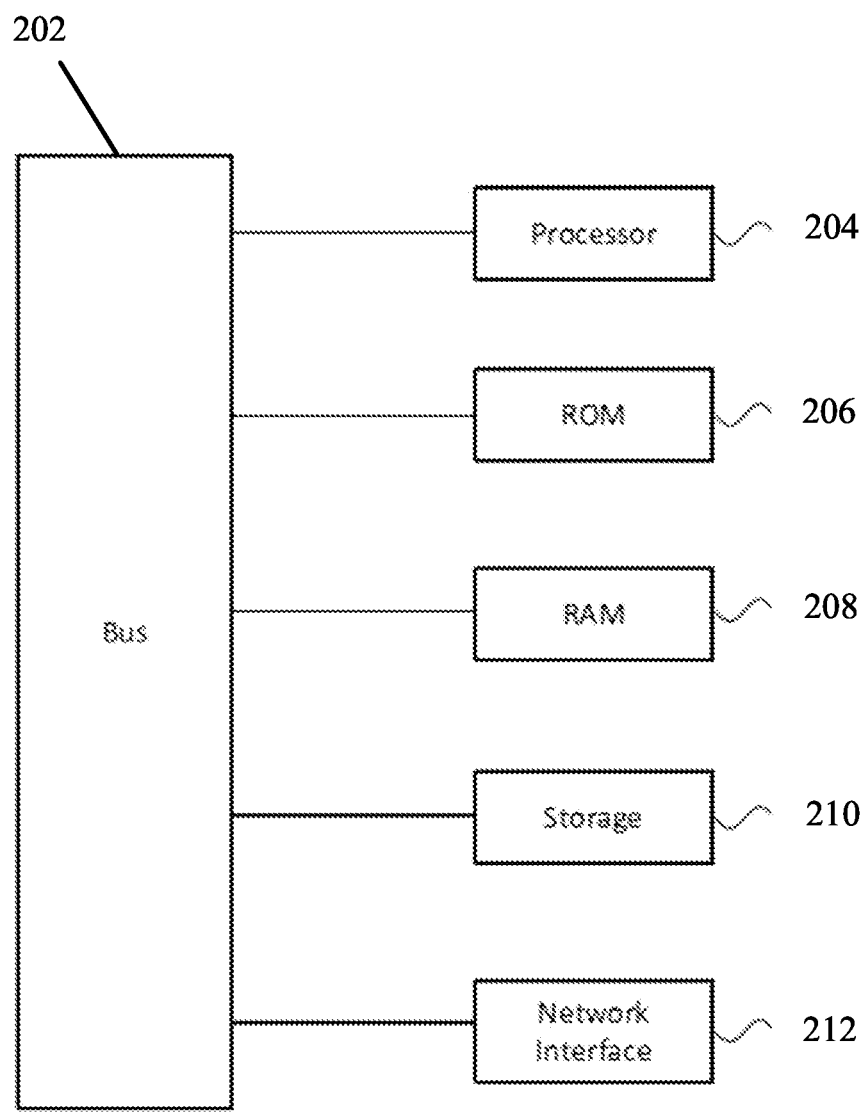
FIG. 2 is a simplified block diagram of one or more devices or systems within the exemplary environment of FIG. 1A according to one or more examples of the present application.

FIG. 2 is a simplified block diagram of one or more devices or systems within the exemplary environment of FIG. 1A according to one or more examples of the present application. For instance, the device/system 200 may be the personalized erythropoiesis computing system 108 and/or the user device 110 of FIG. 1A. The device/system 200 includes a processor 204, such as a central processing unit (CPU), controller, and/or logic, that executes computer executable instructions for performing the functions, processes, and/or methods described herein. In some examples, the computer executable instructions are locally stored and accessed from a non-transitory computer readable medium, such as storage 210, which may be a hard drive or flash drive. Read Only Memory (ROM) 206 includes computer executable instructions for initializing the processor 204, while the random-access memory (RAM) 208 is the main memory for loading and processing instructions executed by the processor 204. The network interface 212 may connect to a wired network or cellular network and to a local area network or wide area network, such as the network 106. The device/system 200 may also include a bus 202 that connects the processor 204, ROM 206, RAM 208, storage 210, and/or the network interface 212. The components within the device/system 200 may use the bus 202 to communicate with each other. The components within the device/system 200 are merely exemplary and might not be inclusive of every component, server, device, computing platform, and/or computing apparatus within the device/system 200. Additionally, and/or alternatively, the device/system 200 may further include components that might not be included within every entity of environment 100.

Figure 3:
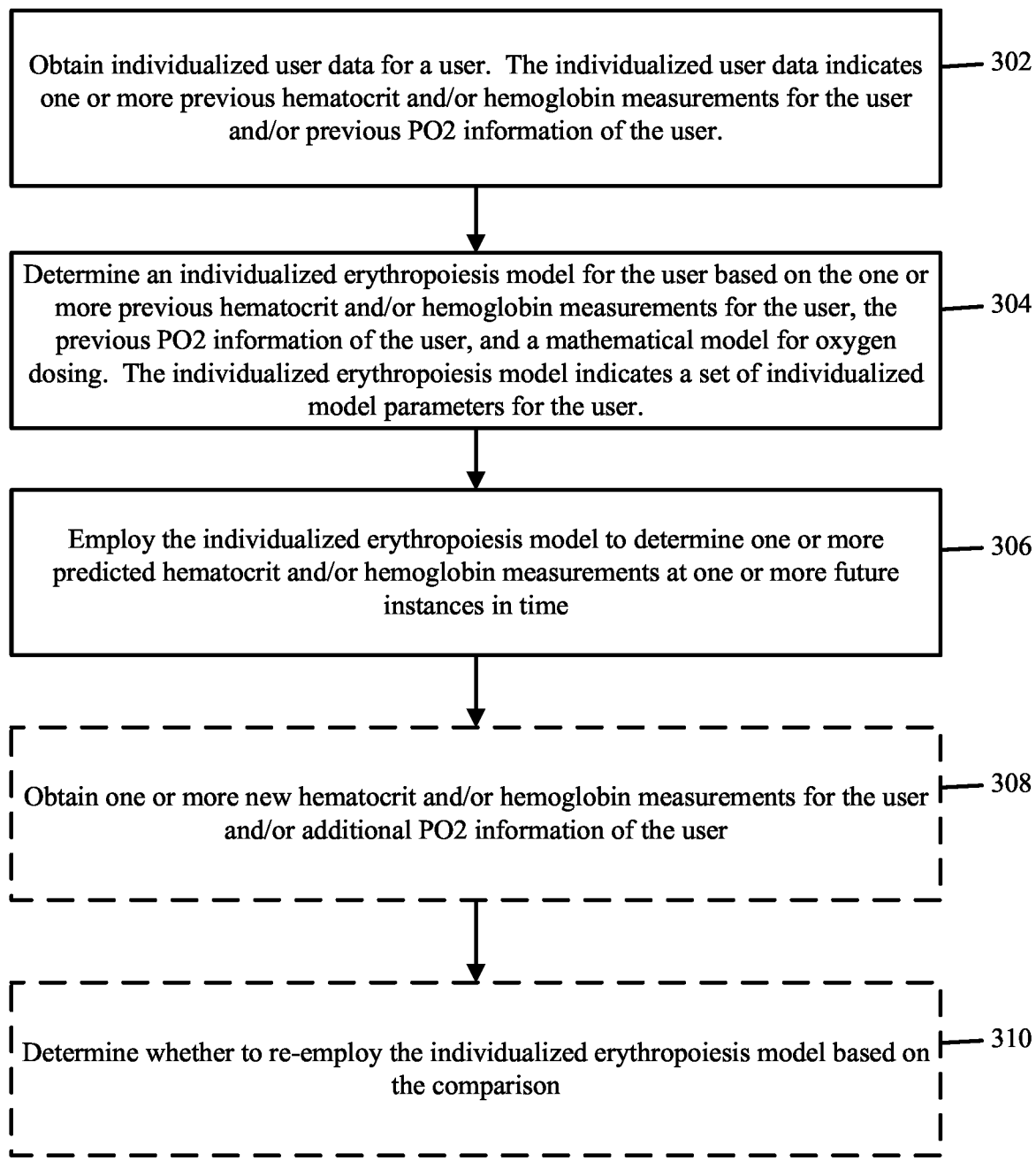
FIG. 3 is a flowchart of an exemplary process for monitoring a user's hematocrit and/or hemoglobin concentration using an individualized erythropoiesis model according to one or more examples of the present application.

FIG. 3 is a flowchart of an exemplary process 300 for monitoring a user's hematocrit and/or hemoglobin concentration using an erythropoiesis model according to one or more examples of the present application. The process may be performed by a computing device such as the user device 110 and/or the personalized erythropoiesis model generation computing system 108 depicted in FIG. 1A. However, it will be recognized that any of the following blocks may be performed in any suitable order, and that the process 300 may be performed in any suitable environment and by any suitable device or system. The descriptions, illustrations, and processes of FIG. 3 are merely exemplary and the process 300 may use other descriptions, illustrations, and processes for monitoring a user's hematocrit and/or hemoglobin concentrations.

For example, in some variations, a computing device (e.g., the computing system 108 and/or the user device 110) may obtain individualized user data for a user (e.g., a particular user's previous low oxygen events, previous hematocrit/hemoglobin measurements, previous erythropoietin level measurements of the user, gender, weight, altitude at which the user resides at normally, and/or other characteristics of the user). The computing device may determine a user specific erythropoiesis model (e.g., an individualized erythropoiesis model) for the user based on the individualized user data (e.g., user-individual data).

In some examples, the computing device may initially use a generalized erythropoiesis model based on the user characteristics (e.g., the user's gender or weight). For instance, the computing device or a separate computing entity may generate a generalized erythropoiesis model based on population data associated with a plurality of users. Then, the computing device may obtain the generalized erythropoiesis model and modify/adjust the generalized erythropoiesis model to be more tailored to the user (e.g., generate the individualized erythropoiesis model). This will be described in further detail in FIG. 4.

At block 302, the computing device (e.g., the computing system 108 and/or the user device 110) obtains individualized user data for a user. The individualized user data indicates one or more previous hematocrit and/or hemoglobin measurements for the user and/or previous PO2 information of the user. For instance, in some examples, the user device 110 may generate the previous PO2 information of the user, and provide the generated previous PO2 information of the user to the computing system 108. For example, referring to FIG. 1B, the user device 110 may use one or more sensors to measure PO2 levels over a period of time. Using the measurements, the user device 110 may generate the previous PO2 information, which may include one or more low oxygen events over the period of time. Furthermore, as shown, the low oxygen events may be at different PO2 levels. Examples of low oxygen events include high altitude events, hypoxic chambers to simulate high altitude conditions, elevation training masks, and so on. In some instances, the computing system 108 and/or the user device 110 may receive the hemoglobin and/or hematocrit measurement levels from the external measurement system 104. For instance, the external measurement system 104 may be associated with a blood lab that is configured to measure hemoglobin and/or hematocrit measurement levels of the users' blood and provide the measured values to the computing system 108 and/or the user device 110.

Additionally, and/or alternatively, the individualized user data may include, but is not limited to, hemoglobin, hematocrit, mean corpuscular hemoglobin content, erythropoietin levels, gender, height, weight, altitude of residency, smoking status, clinical parameters such as oxygen saturation, treatment time, bleeding events, blood transfusions, hospitalizations, diseases and/or life style choices of the user that changes the oxygen binding to HGB, and so on for the user.

In some examples, the previous hematocrit and/or hemoglobin measurement for the user may indicate multiple different hematocrit and/or hemoglobin measurements. For instance, the user may seek to attain specific heightened hemoglobin level (e.g., a HGB target) at a predefined point in time, and may undergo repetitive low oxygen events. The user device 110 and/or the external measurement system 104 may obtain and/or determine hemoglobin levels before, during, and after the low oxygen event in order to measure the user's response to hemoglobin and/or EPO in response to these perturbations.

At block 304, the computing device determines an individualized erythropoiesis model for the user based on the one or more previous hematocrit and/or hemoglobin measurements for the user, the previous PO2 information of the user, and a mathematical model for oxygen dosing (e.g., the mathematical model described below in FIG. 5). The individualized erythropoiesis model indicates a set of individualized model parameters (e.g., an individualized virtual avatar) for the user. For instance, the set of individualized model parameters may be values, functions, or constants associated with the variables of the mathematical model. For example, the mathematical model, which is described in further detail in FIG. 5, includes a plurality of mathematical equations and user parameters (e.g., variables). The computing device may use the individualized user data to determine the user parameters (e.g., variables) for the mathematical model. To put it another way, each user and/or group of users (e.g., a group of users with similar user characteristics such as weight, height, gender, and so on) may react slightly differently to low oxygen events. As such, a first user and/or group of users performing a low oxygen event may have different impacts (e.g., different hematocrit/hemoglobin concentration levels) from another user and/or group of users. The mathematical model may be associated with a first set of variables that are not user/group specific and a second set of variables that are user/group specific. The second set of variables may be the set of individualized model parameters that are indicated by the virtual user avatars. Accordingly, the computing device generates an individualized virtual avatar by inputting the individualized user data (e.g., the previous hemoglobin/hematocrit measurements and/or the previous PO2 information) into the mathematical model to determine the set of individualized model parameters.

The set of individualized parameters for the user may include, but are not limited to, production of the hormone EPO, the RBC lifespan, the parameters indicating user-specific magnitude of the hemoglobin and EPO response to a low oxygen event, parameters indicating the user's base hemoglobin levels in the absence of a pharmacologic therapy for anemia, and/or iron related parameters.

The partial pressure ($p_{O_2}$) may be described in Eq. (1.7) below. For example, the partial pressure may be associated with the PO2 information (e.g., the previous PO2 information obtained at block 302). For instance, the partial pressure may be a time series function of the PO2 information (e.g., a time series function of the graphical representation 150).

The RBC lifespan ($\kappa_{ery}^{-1}$) may be described in Eq. (1.17) below. The RBC lifespan may indicate the lifespan of red blood cells for the users. For instance, the computing device may determine the RBC lifespan based on the apoptosis rates for the cell population, the EPO for downregulation of progenitor apoptosis, the basal EPO production, and/or the rate of neocytolysis regulated by the hormone EPO. The RBC lifespan may indicate the average life span of a red blood cell.

The set point for the concentration of oxygenated hemoglobin in blood ($\sigma_{O_2}^*$) may be described in Eq. (1.6) and Eq. (1.7) below. For instance, the computing device may determine this set point based on the blood hemoglobin concentration as measured by the kidneys, the number of erythrocytes, activation and inhibition functions, the hypoxic upregulation of the HIF signal in response to decreases in the concentration of oxygenated hemoglobin in blood, the upregulation of the HIF signal in response to hypoxic conditions, the decay rate of the HIF signal, and/or other factors. The HB set point may be defined as the blood HB concentration at which the activity of endogenous feedbacks such as upregulating or downregulating RBC generation is minimal.

The basal EPO synthesis rate ($\beta_e$) may be described in Eq. (1.8) below. For instance, the computing device may determine the basal EPO synthesis rate based on the serum EPO concentration, the EPO synthesis, and/or the EPO decay rate. The basal EPO synthesis rate may indicate the rate at which EPO is synthesized in the body.

The individualized model parameters may further include additional model parameters. For instance, input conditions, limits, and/or options for a systematic training strategy may be input into the model. For example, the additional model parameters may include, but are not limited to, a desired total length of time available to apply controlled hypoxic conditions, a maximum possible drop in PO2, earliest and latest possible time points for low oxygen events ahead of the target time point at which desired HGB levels should be reached, and so on.

Additionally, and/or alternatively, another model parameter may be a timing to the performance event (e.g., marathon, competition, race) for desired peak hemoglobin level. Another model parameter may include an oxygen lowering method. For example, some individuals may not have access to a hypoxic chamber but may live close to the mountains. Or, some individuals may not have access to a hypoxic chamber nor the mountains. Some individuals may have access to a hypoxic chamber or the mountains, but only a limited frequency (e.g., on the weekends). These individualized constraints can be input so the systematic training strategy generated accounts for these, which will be described below. In some examples, the elevation of the available high-altitude training may also be a model parameter. Another model parameter may be the duration of the peak hemoglobin level. For example, some individuals may be looking to maximize their hemoglobin level for a single event that last one day. Other individuals may be looking to maximize their hemoglobin level for a longer period, for example, a bike race that last several days or even weeks.

To generate the individualized model parameters, the computing device may systematically fit (e.g., assign) a specified set of model parameters to the individualized user data using inputs (e.g., previous low oxygen event data). Then, the computing device determines the "goodness" of a fit based on deviations between the simulated and measured hemoglobin/hematocrit concentrations (e.g., between the hemoglobin/hematocrit concentrations output by the individualized erythropoiesis model using the assigned set of model parameters and the actual hemoglobin/hematocrit concentrations from the individualized user data). The computing device may use a cost function to define the goodness of the fit, and the fitting procedure may be performed using one or more parameter fit algorithms. In some examples, other pairs of simulated and measured data elements (e.g., erythropoietin serum concentrations, iron plasma concentrations, and so on) may also be used to determine the goodness of the fit.

In other words, the computing device may assign values to the set of model parameters described above (e.g., the partial pressure, RBC lifespan, set point for the concentration of oxygenated hemoglobin in blood, basal EPO synthesis rate, and/or additional model parameters). Subsequently, the computing device may determine (e.g., obtain/use) previous low oxygen events (e.g., the previous PO2 information) and previous hemoglobin/hematocrit concentrations. Then, the computing device may input the previous low oxygen events and the assigned set of model parameters into the mathematical model to determine simulated hemoglobin/hematocrit concentrations. The computing device may compare the simulated hemoglobin/hematocrit concentrations with the actual hemoglobin/hematocrit concentrations to determine deviations between the two. Afterwards, the computing device may assign new values to the set of model parameters and repeat the process. The computing device may continuously assign new values to the set of model parameters and determine deviations between the simulated hemoglobin/hematocrit concentrations with the actual hemoglobin/hematocrit concentrations. For instance, the computing system 108 may use the previously computed deviations to determine which new values to try in the next iteration. In other words, the computing device may use one or more parameter fit algorithms (e.g., optimization of one or more distance measurements between the simulated and actual concentrations) to determine the best set of model parameters for the subset of population user data. The computing device may determine the set of model parameters for the virtual user avatar as the best set of model parameters. For instance, the computing device may compare the distance between the simulated and actual hemoglobin/hematocrit concentrations and use the set of model parameters that produced the smallest distance between the simulated and actual concentrations.

In some examples, the computing device may use the low oxygen events and/or other information (e.g., patient characteristics such as gender, height weight, blood volume, and so on) to determine the individualized erythropoiesis model for the user.

In some variations, the computing device may select the individualized erythropoiesis model for the user from one of a plurality of virtual patient avatars. For instance, each of the plurality of virtual user avatars may be associated with a subset of users (e.g., based on a user's height, weight, gendered, and so on). Based on comparing the individualized user data with subsets of population user data, the computing device may determine the virtual user avatar that most resembles the user based on the individualized user data (e.g., the virtual user avatar that has the same or similar user characteristics such as height, weight, gender, low oxygen events, hemoglobin concentration measurements, and so on). This will be described in further detail in FIG. 4.

At block 306, the computing device employs the individualized erythropoiesis model to determine one or more predicted hematocrit and/or hemoglobin measurements at one or more future instances in time. For instance, the computing device may input data (e.g., measured hematocrit and/or hemoglobin levels of the user) into the individualized erythropoiesis model, and the output of the individualized erythropoiesis model may be one or more predicted hematocrit and/or hemoglobin measurements at one or more future instances in time. In some instances, the one or more predicted hematocrit and/or hemoglobin measurements may include the desired hematocrit and/or hemoglobin measurements at the occurrence of the performance event. Additionally, and/or alternatively, the one or more predicted hematocrit and/or hemoglobin measurements may include one or more interim hematocrit and/or hemoglobin measurements (e.g., checkpoint hematocrit and/or hemoglobin measurements) indicating checkpoints for the user to achieve in their goal to reach the desired hematocrit and/or hemoglobin measurements. For instance, the checkpoint hematocrit and/or hemoglobin measurements may be 50% and 75% of the desired hematocrit and/or hemoglobin measurements.

Subsequently, the computing device may display information associated with the predicted hematocrit and/or hemoglobin measurements (e.g., the checkpoints hematocrit and/or hemoglobin measurements and/or the desired hematocrit and/or hemoglobin measurements). Additionally, and/or alternatively, the computing device may employ the individualized erythropoiesis model to generate a systematic training strategy (e.g., determine one or more first low oxygen events for the user to perform). For instance, after determining the individualized erythropoiesis model at block 304, the computing device may generate a plurality of future PO2 information (e.g., a plurality of time series functions with low oxygen events). The future PO2 information may indicate the systematic training strategy. In other words, the previous PO2 information obtained at block 302 may indicate low oxygen events that have already been experienced by the user (e.g., low oxygen events experienced by the user in the past month). The future PO2 information may indicate low oxygen events for the user to complete in the future (e.g., to complete in the next two months) to reach a desired hematocrit and/or hemoglobin measurement at the occurrence of the performance event. For instance, the future PO2 information may indicate one or more low oxygen events for the user to perform, and each low oxygen event may indicate a PO2 level and a time period or time instance. The computing device may input each of the future PO2 information into the individualized erythropoiesis model and the individualized erythropoiesis model may output a predicted hematocrit and/or hemoglobin measurement at a future instance in time. Then, the computing device may compare the predicted hematocrit and/or hemoglobin measurement with a desired hematocrit and/or hemoglobin measurement for the user (e.g., a desired hematocrit and/or hemoglobin measurement to be obtained by the time of the performance event). Based on the comparison, the computing device may determine the most optimal future PO2 information (e.g., the future PO2 information with a predicted hematocrit and/or hemoglobin measurement that is closest to the desired hematocrit and/or hemoglobin measurement). Subsequently, the computing device may determine the systematic training strategy associated with the future PO2 information. For instance, the systematic training strategy may indicate the low oxygen events for the user to perform in the upcoming time period prior to the performance event. The computing device may display the systematic training strategy.

In some instances, the computing device may determine the systematic training strategy based on the individualized constraints for the user. For instance, each user may be unique and may be able to handle constraints differently from other users. For example, a healthy user may be able to handle being at a higher PO2 level for a longer period of time whereas a user that is less healthy might not be able to do so. The individualized constraints may include any characteristics, features, or metrics associated with the user that may be used to optimize the systematic training strategy. For instance, the individualized constraints may include, but are not limited to, the overall time that a user can spend in a chamber or at an elevated altitude, a time that the user has for training, the PO2 values (e.g., a range) that the user can experience, the maximum or minimum PO2 levels that a user can be exposed to, or other types of individualized constraints. The computing device may use the individualized constraints to optimize the systematic training. For instance, based on the computing device that determines the most optimal future PO2 information is outside of the individualized constraints for the user (e.g., the most optimal future PO2 information indicates a maximum or minimum PO2 level that is outside of the user's maximum or minimum PO2 level indicated by the individualized constraints), the computing device may reject the most optimal future PO2 information and select a different future PO2 information for the user (e.g., the second or third most optimal future PO2 information that has metrics within the individualized constraints of the user).

In some instances, process 300 may end after block 306. In other instances, process 300 may further include blocks 308 and 310, which describe re-employing the individualized erythropoiesis model. In other words, blocks 308 and 310 include dashed lines to indicate that these blocks are optional in process 300.

When performed, at block 308, the computing device obtains one or more new hematocrit and/or hemoglobin measurements for the user and/or additional PO2 information of the user. The additional PO2 information may indicate one or more low oxygen events that the user has performed since the individualized erythropoiesis model was employed in block 306. At block 310, the computing device determines whether to re-employ the individualized model.

For example, the computing device may determine whether to re-employ the individualized erythropoiesis model for the user at a later instance in time. For instance, a performance event (e.g., an athletic event or surgery) may occur a certain amount of time in the future (e.g., 2 months in the future), and the user may seek to reach a desired hematocrit and/or hemoglobin level at that time. The computing device may initially perform blocks 302-306 to determine the future PO2 information and/or predicted hematocrit and/or hemoglobin measurements. Then, after a period of time elapses (e.g., after one month), the computing device may perform blocks 308 and 310 to determine whether to re-employ the individualized erythropoiesis model. For instance, the user may have one or more setbacks such that they were unable to perform one or more low oxygen events indicated by the future PO2 information. As such, after a month of the two months until the performance event occurs has elapsed, the computing device may perform blocks 308 and 310 to determine an updated future PO2 information such that the user is still capable of meeting the desired hematocrit and/or hemoglobin measurement at the time the performance event occurs. For instance, after a period of time (e.g., a month), the computing device may obtain one or more new hematocrit and/or hemoglobin measurements for the user and/or additional PO2 information. The additional PO2 information may include the previous PO2 information of the user as well as new PO2 information (e.g., new low oxygen events) that the user has experienced since employing the individualized erythropoiesis model at block 306. The computing device may compare the new hematocrit and/or hemoglobin measurements with the one or more predicted hematocrit and/or hemoglobin measurements from block 306 (e.g., one or more checkpoint hematocrit and/or hemoglobin measurements). Based on the comparison, the computing device may determine whether to re-employ the individualized erythropoiesis model. For instance, based on the computing device determines that the new hematocrit and/or hemoglobin measurements are within a certain threshold of the predicted hematocrit and/or hemoglobin measurements (e.g., plus or minus 5% away from the predicted hematocrit and/or hemoglobin measurements), the computing device may determine not to re-employ the individualized erythropoiesis model.

Based on the computing device determining that the new hematocrit and/or hemoglobin measurements are outside the certain threshold, the computing device may determine to re-employ the individualized erythropoiesis model. In some instances, by re-employing the individualized erythropoiesis model, the computing device may determine one or more new predicted hematocrit and/or hemoglobin measurements and/or updated future PO2 information. The new predicted hematocrit and/or hemoglobin measurements and/or the updated future PO2 information may be used to assist the user in reaching their desired hematocrit and/or hemoglobin measurements by the occurrence of the performance event.

In some variations, one or more blocks of process 300 may repeat. For example, blocks 308 and 310 may repeat one or more times prior to reaching the occurrence of the performance event. For instance, after a set amount of time (e.g., every week or every few days), the computing device may obtain new hematocrit and/or hemoglobin measurements for the user and the additional PO2 information. The computing device may then employ the individualized erythropoiesis model as many times as desired. For instance, as mentioned above, the user device 110 may include one or more sensors that are configured to continuously obtain PO2 information for the user. As such, after a certain time has elapsed, the user device 110 may provide the additional PO2 information from the sensors to the computing system 108, and the computing system 108 may re-employ the individualized erythropoiesis model.

In some instances, in the event of iron deficiency of the user, the computing device may use iron intake as a parameter for the individualized erythropoiesis model.

Figure 4:
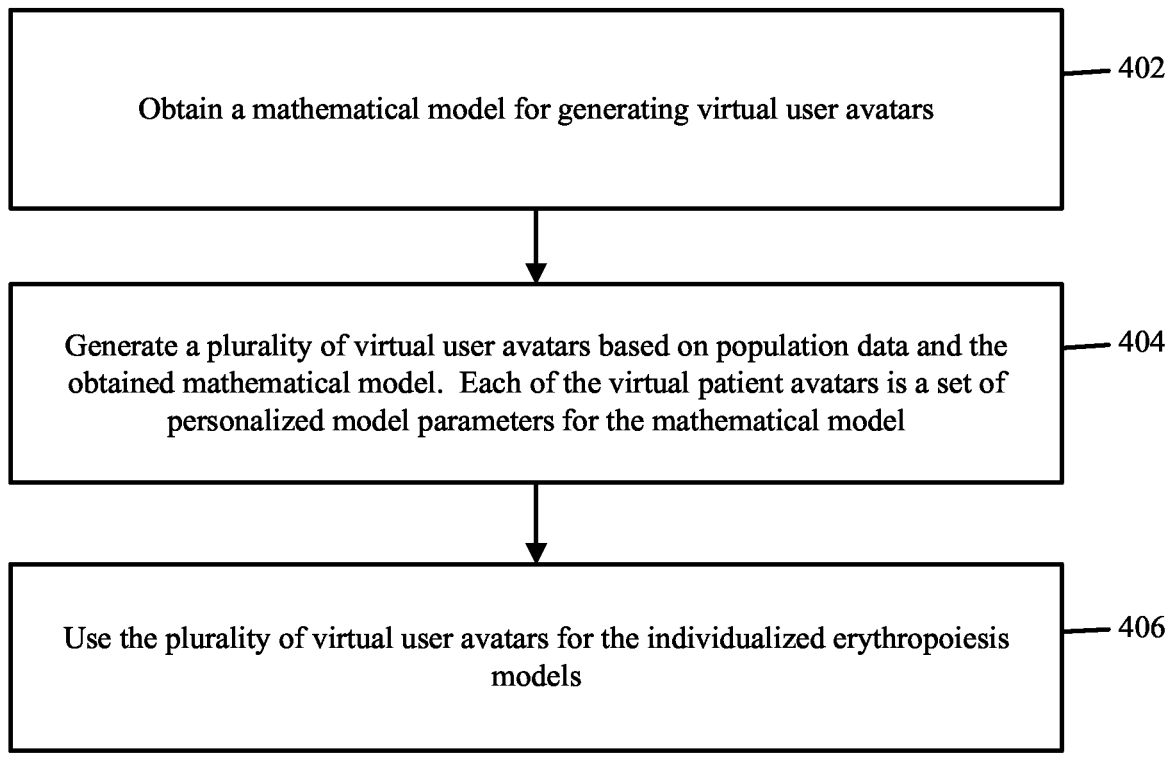
FIG. 4 is a flowchart of an exemplary process for generating erythropoiesis models according to one or more examples of the present application.

FIG. 4 is a flowchart of an exemplary process 400 for generating erythropoiesis models according to one or more examples of the present application. The process may be performed by a computing device such as the personalized erythropoiesis model generation computing system 108 and/or the user device 110 depicted in FIG. 1A. However, it will be recognized that any of the following blocks may be performed in any suitable order, and that the process 400 may be performed in any suitable environment and by any suitable device or system. The descriptions, illustrations, and processes of FIG. 4 are merely exemplary and the process 400 may use other descriptions, illustrations, and processes for generating the erythropoiesis models.

For example, in some instances, the individualized user data may be missing certain data points, which may cause it to not be sufficient enough to determine an individualized erythropoiesis model. Additionally, and/or alternatively, the user may be part of a group of users with similar features or goals (e.g., a team of soccer players, a group of users that have an upcoming triathlon, or a group of users with similar physiques). As such, the computing device may generate virtual user avatars for the group of users.

Figure 5A:
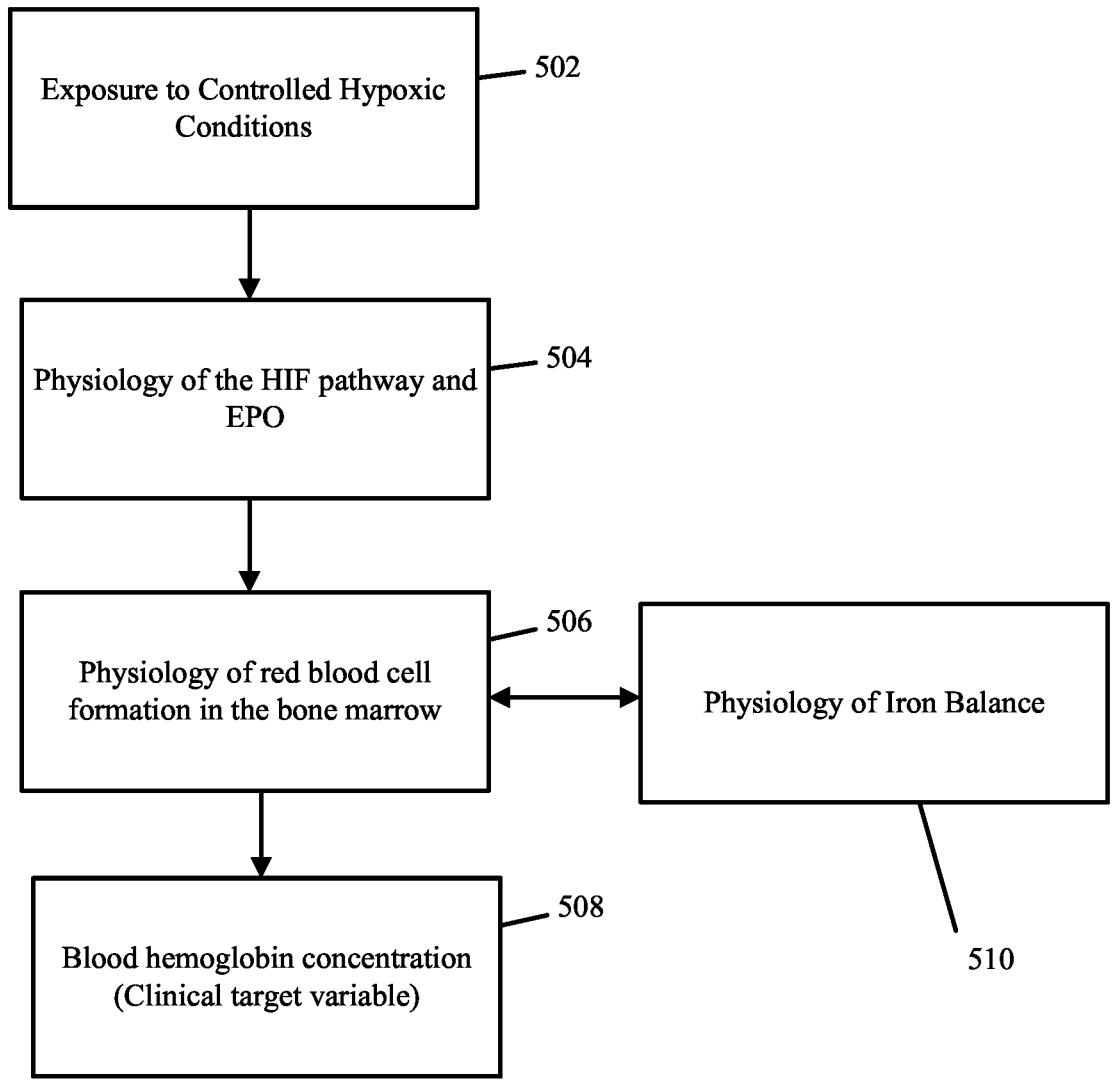
FIG. 5A is a block diagram of the exemplary mathematical erythropoiesis model according to one or more examples of the present application.

At block 402, the computing device obtains a mathematical model for generating virtual user avatars. For example, the computing device may receive the mathematical model (e.g., a mathematical model for oxygen dosing) from another entity (e.g., a server or computing system associated with an enterprise organization). Additionally, and/or alternatively, the mathematical model may be stored in memory (e.g., external memory or memory within the computing system 108) and the computing device may retrieve the mathematical model from the memory. FIG. 5A shows an exemplary mathematical model 500 for monitoring a user's hemoglobin or hematocrit level that may be obtained by the computing device, and will be described in further detail below.

At block 404, the computing device generates a plurality of virtual user avatars based on population user data (e.g., historical data and/or simulated data for a plurality of users) and the obtained mathematical model. Each of the virtual user avatars is a set of personalized model parameters for the mathematical model. The population user data may be historical data of a plurality of users and/or simulated data of a plurality of users. For example, the population user data may include, but is not limited to, hemoglobin, hematocrit, erythropoietin serum, gender, height, weight, clinical parameters such as oxygen saturation, treatment time, bleeding events, blood transfusions, hospitalizations, and so on for a plurality of users. The population user data may be over a specified time window (e.g., a certain time period).

The computing device may generate virtual user avatars, which are a set of personalized model parameters, for the obtained mathematical model. For example, the mathematical model, which is described in further detail in FIG. 5A, includes a plurality of mathematical equations and user parameters (e.g., variables). The computing device may use the population user data to determine user parameters (e.g., variables) for the mathematical model. To put it another way, each user and/or group of users (e.g., a group of users with similar user characteristics such as weight, height, gender, and so on) may react slightly differently to low oxygen events. As such, a first user and/or group of users performing a low oxygen event may have different impacts (e.g., different hematocrit/hemoglobin concentration levels) from another user and/or group of users. The mathematical model may be associated with a first set of variables that are not user/group specific and a second set of variables that are user/group specific. The second set of variables may be the set of personalized model parameters that are indicated by the virtual user avatars. Accordingly, the computing device generates virtual user avatars by inputting the population user data into the mathematical model to determine the set of personalized model parameters.

The set of personalized model parameters associated with each virtual user avatar may be similar to the set of individualized model parameters described above in FIG. 3 except that they are for a group of users rather than a single user. As such, each virtual user avatar may indicate a set of personalized model parameters for a particular group, and the computing device may generate a plurality of these virtual user avatars. To generate the virtual user avatars, the computing device may systematically fit (e.g., assign) a specified set of model parameters to the population user data using inputs (e.g., previous low oxygen event data). Then, the computing device determines the "goodness" of a fit based on deviations between the simulated and measured hemoglobin/hematocrit concentrations (e.g., between the hemoglobin/hematocrit concentrations output by the erythropoiesis model using the assigned set of model parameters and the actual hemoglobin/hematocrit concentrations from the population user data). The computing device may use a cost function to define the goodness of the fit, and the fitting procedure may be performed using one or more parameter fit algorithms. In some examples, other pairs of simulated and measured data elements (e.g., erythropoietin serum concentrations, iron plasma concentrations, and so on) may also be used to determine the goodness of the fit.

In other words, the computing device may determine a subset of population user data based on certain characteristics (e.g., height, weight, gender, and so on). The computing device may assign values to the set of model parameters described above. Subsequently, the computing device may determine previous low oxygen events and hemoglobin/hematocrit concentrations within the subset of population user data. Then, the computing device may input the previous low oxygen events and the assigned set of model parameters into the mathematical model to determine simulated hemoglobin/hematocrit concentrations. The computing device may compare the simulated hemoglobin/hematocrit concentrations with the actual hemoglobin/hematocrit concentrations to determine deviations between the two. Afterwards, the computing device may assign new values to the set of model parameters and repeat the process. The computing device may continuously assign new values to the set of model parameters and determine deviations between the simulated hemoglobin/hematocrit concentrations with the actual hemoglobin/hematocrit concentrations. For instance, the computing system 108 may use the previously computed deviations to determine which new values to try in the next iteration. In other words, the computing device may use one or more parameter fit algorithms (e.g., optimization of one or more distance measurements between the simulated and actual concentrations) to determine the best set of model parameters for the subset of population user data. The computing device may determine the set of model parameters for the virtual user avatar as the best set of model parameters. For instance, the computing device may compare the distance between the simulated and actual hemoglobin/hematocrit concentrations and use the set of model parameters that produced the smallest distance between the simulated and actual concentrations.

The computing device may determine a plurality of virtual user avatars based on using subsets of the population data and each of the plurality of virtual user avatars may be associated with certain user characteristics (e.g., gender, weight, height) and a set of personalized model parameters.

In some instances, the computing device may perform pre-calibrating functions prior to generating the virtual user avatars. For instance, the computing device may determine blood volumes based on the subset of population user data. For example, using the gender, height, weight, and/or other information from the subset of population user data, the computing device may determine a blood volume for the virtual user avatar. Then, using the blood volume, the computing device may determine rates such as formation rates, synthesis rates, and/or other rates for the virtual user avatar. For instance, the computing device may determine the HIF signaling gain rate (shown as $\beta_h$ in Eq. (1.6) below), the EPO synthesis rate (shown as $\beta_e$ in Eq. (1.8) below), the progenitor formation rate (shown as $\beta_{prog}$ in Eq. (1.9) below). The computing device may use the determined rates, the assigned set of model parameters, the previous low oxygen events, the mathematical model, and/or other data to determine simulated hemoglobin/hematocrit concentrations. Then, based on the simulated hemoglobin/hematocrit concentrations, the computing device may determine a best set of model parameters to use for the virtual user avatar.

In some variations, in addition to the simulated hemoglobin/hematocrit concentrations, the computing device may further use the mathematical model, the previous low oxygen events, and/or other information to determine the EPO (shown as the variable "e" in Eq. (1.8)) and/or other simulated data points. The computing device may further obtain the EPO and/or other data points from the subset of population user data. The computing device may compare the simulated and actual data points, and use the one or more parameter fit algorithms to determine the best set of model parameters to use for the virtual user avatar.

At block 406, the computing device uses the plurality of virtual user avatars to determine the individualized erythropoiesis model. For instance, as mentioned above in block 304 of FIG. 3, based on comparing the individualized user data with subsets of population user data, the computing device may determine the virtual user avatar that most resembles the user based on the individualized user data (e.g., the virtual user avatar that has the same or similar user characteristics such as height, weight, gender, low oxygen events, hemoglobin concentration measurements, and so on). Then, the computing device may update the personalized model parameters of the virtual user avatar using the individualized user data. For instance, the computing device may change one or more of the personalized model parameters based on comparing the obtained hemoglobin concentration of the user with simulated hemoglobin concentrations output by the erythropoiesis model. In some instances, the computing device may use the parameters indicated by the determined virtual user avatar as the individualized erythropoiesis model.

FIG. 5A is a block diagram of an exemplary mathematical model 500 according to one or more examples of the present application. As mentioned previously, the mathematical model 500 may be used to determine/generate the plurality of virtual user avatars, determine the individualized erythropoiesis model for the user, and/or determine the timing and magnitude of low oxygen events of the user to adjust the user's hematocrit/hemoglobin concentrations (e.g., the future PO2 information).

For example, block 502 is the exposure to controlled hypoxic conditions. For instance, as mentioned previously, the computing system 108 may obtain the exposure to the controlled hypoxic conditions (e.g., PO2 information such as previous and/or additional PO2 information) of the user. The PO2 information may be a time series of PO2 levels of the user over a period of time such as shown in graphical representation 150 of FIG. 1B.

Block 504 of the mathematical model 500 is the physiology of the HIF pathway and the erythropoietin (EPO). For instance, HIFs (hypoxia-inducible factors) are constitutively expressed transcription factors that elicit the response to decreased available oxygen levels by upregulating the expression of various target genes. The HIF transcriptional complex is a heterodimer of its subunits HIF-α and HIF-β.

There are three isoforms of HIF-α termed HIF-1α, HIF-2α and HIF-3α. Under normoxic conditions, HIF-α is located in the cytoplasm; HIF-β is located in the nucleus. As $O_2$ concentration decreases, HIF-α (specifically, the isoform HIF-2α) is stabilized, translocates to the nucleus and binds to HIF-β to form the HIF transcriptional complex. The HIF complex regulates the transcription of target genes like EPO in kidney and liver. This is achieved by binding to hypoxia-responsive elements (HREs) in the respective gene promoters.

The HIF pathway includes multiple biochemical species such as HIF-α and HIF-β as well as the dimer that they form. To reduce model complexity, a single composite variable h is introduced that represents the "HIF signal". More precisely, let $n_{cmp}$ denote the amount of HIF transcriptional complexes bound to EPO promoter regions and $n^*_{cmp}$ denote its average under normoxic conditions, then h can be defined by $h(t) \sim n_{cmp}(t) - n^*_{cmp}$.

Hence, the sign of h depends on whether $n_{cmp}$ takes value above or below the steady state baseline level $n^*_{cmp}$.

In healthy patients, the HIF signal is upregulated in the presence of hypoxia via the feedback in the kidneys. Here, a set point $\sigma_{O_2}^*$ for the concentration of oxygenated hemoglobin in blood is considered; the HIF signal reacts to any deviation from the set point. Moreover, since hypoxia prevents HIF-α degradation via a decrease in proline hydroxylation, they effectively upregulate the amount of available HIF complexes that are able to bind EPO promoters. Therefore, h is upregulated under hypoxic conditions. These contributions are combined in the following equations (1.6) and (1.7).

$$\frac{dh}{dt} = \beta_h(\theta)\varphi_{a_h,b_h,q_{h,0}}\left(k_h\left[\sigma_{O_2} - \sigma_{O_2}^*\right]\right) - k_h h, \qquad \text{Eq. (1.6)}$$

where $$\sigma_{O_2} = S(c_{hgb}, p_{O_2}) \qquad \text{Eq. (1.7)}$$

$\sigma_{O_2}$ denotes the concentration of oxygenated hemoglobin in blood as measured by the kidneys, which is a function of the hemoglobin concentration $c_{hgb}$ (a derived model variable, see Eq. (D)) and the O2 partial pressure $p_{O_2}$. Furthermore, $\sigma_{O_2}^*$ denotes the physiological set point for the concentration of oxygenated hemoglobin in blood and $\beta_h(\theta)$ denotes the formation rate of HIF complexes. Functions of the type $\varphi$ and $\phi^-(x)$ (shown below) are sigmoidal functions describing non-linear activation and inhibition, and the first term ($\varphi_{a_h,b_h,q_{h,0}}$) describes the hypoxic upregulation of the HIF signal in response to decreases in the blood hemoglobin concentration. The functions $\varphi$ and $\phi^-(x)$ are defined as follows:

$$\phi^-(x) = \frac{1}{1+x} \qquad \text{Eq. (A)}$$

$$\varphi_{a,b,q}(x) = a + \frac{b-a}{1-qe^{-x}} \qquad \text{Eq. (B)}$$

where x is an input variable and a, b and q are shape parameters determining the offset, height and steepness of the function. Eq. (A) may be referred to as a Hill type function. Eq. (B) may be referred to as a Richards type equation.

Referring back to Eq. (1.6), the parameter k h denotes the decay rate of the HIF signal. In other words, $$\frac{dh}{dt}$$

indicates a rate or change of HIF signaling activity, $\beta_h(\theta)$ indicates a formation rate of HIF complexes, $\varphi_{a_h,b_h,q_{h,0}}$ indicates a hypoxic upregulation of a HIF signal in response to decreases in the concentration of oxygenated hemoglobin in blood, $k_h$ indicates a decay rate of the HIF signal, $\sigma_{O_2}$ indicates a concentration of oxygenated hemoglobin in blood measured by kidneys, $\sigma_{O_2}^*$ indicates a physiological set point for the concentration of oxygenated hemoglobin in blood, and h indicates the HIF signal. The function S is considered to be of the form $$S(c_{hgb}, p_{O_2}) = c_{hgb} \frac{(p_{O_2}/p_{O_2}^*)^{r_S}}{1 + (p_{O_2}/p_{O_2}^*)^{r_S}} \quad \text{Eq. (C)}$$

where the second term describes a sigmoidal dependence of the fraction of oxygenated hemoglobin in blood on inspiratory PO2, which describes the net effect of a monotonically increasing dependence of kidney PO2 on inspiratory PO2 and a sigmoidal oxygen dissociation curve. Here, $p_{O_2}^*$ denotes the inspiratory PO2 needed to achieve half-maximum oxygen saturation and $r_S$ is an exponent describing the steepness of the sigmoidal function.

Serum EPO concentration is described by a second variable e, which is upregulated by the HIF signal and decays with a rate $k_e$, $$\frac{de}{dt} = \beta_e(\theta) + \beta_e(\theta)\varphi_{a_e,b_e,q_{e,0}}(k_e h) - k_e e \quad \text{Eq. (1.8)}$$

The first term describes basal EPO synthesis under steady-state conditions. The second term describes additional EPO synthesis due to activation by the HIF signal. The third term describes EPO decay with rate $k_e$. In other words, for Eq. (1.8), $$\frac{de}{dt}$$

indicates a EPO concentration rate of change, $\beta_e(\theta)$ indicates basal erythropoietin (EPO) synthesis under steady-state conditions, $\beta_e(\theta)\varphi_{a_e,b_e,q_{e,0}}(k_e h)$ indicates additional EPO synthesis due to activation by a HIF signal, and $k_e e$ indicates EPO decay with a decay rate $k_e$.

Blocks 506 and 508 of the mathematical model 500 are the physiology of red blood cell formation in the bone marrow and the blood hemoglobin concentration (clinical target variable). In particular, red blood cells (erythrocytes) are continuously generated through the differentiation and proliferation of a hierarchy of stem and progenitor cells. Hematopoietic stem cells (HSCs) are at the apex of the hierarchy. They self-renew, while part of their progeny successively differentiates into more lineage-committed cell types (megakaryocytic-erythroid progenitors, erythroid burst-forming units [BFU-E], erythroid colony-forming units [CFU-E], proerythroblasts, erythroblasts and reticulocytes). This process is regulated through the HIF pathway, which in turn, regulates endogenous EPO production. EPO inhibits apoptosis (cell death) of progenitor cells. The final step (formation of red blood cells) also requires iron.

The erythropoietic lineage in the bone marrow consists of a multitude of different cell types and states. These cell types may be grouped according to whether their cell fates are regulated by EPO or iron, the master regulators in the mathematical model 500. As a result, the population sizes $n_{prog}$, $n_{pre}$ and $n_{ery}$ of three composite cell populations are introduced that represent (i) progenitor populations (colony-forming units-erythroid (CFU-E) and proerythroblasts), (ii) immediate precursors of erythrocytes (erythroblasts and reticulocytes) and (iii) erythrocytes, respectively. To avoid huge numbers, all of these population sizes are normalized such that they denote the average progeny of a representative unit pool of BFU-Es (erythroid burst-forming unit).

In this scheme, apoptosis of the progenitor population is downregulated by EPO. Differentiation of precursors into erythrocytes is limited by iron availability; if not enough iron is available, cells that are primed for differentiation immediately die off, so that the total loss of precursors due to 'attempted' differentiation is constant. The corresponding dynamics is given by the following equations.

$$\frac{dn_{prog}}{dt} = \beta_{prog}(\theta) - J_{prog \to pre} - K_{prog}, \quad \text{Eq. (1.9)}$$

$$\frac{dn_{pre}}{dt} = 2^{d_{prog}} J_{prog \to pre} - J_{pre \to ery} - K_{pre}, \quad \text{Eq. (1.10)}$$

$$\frac{dn_{ery}}{dt} = 2^{d_{pre}} J_{pre \to ery} - K_{ery} \quad \text{Eq. (1.11)}$$

Here, $\beta_{prog}(\theta)$ denotes the progenitor formation rate, which depends on patient specific demographic and physiological parameters $\theta$, including weight, sex, etc. Thus, $\beta_{prog}$ is proportional to the product of the number of available BFU-Es and the rate at which they differentiate. $J_{i \to j}$ denotes the differentiation flux from population i to j (e.g., population progenitor (prog) to precursors (pre) or pre to erythrocytes (ery)), $K_i$ (e.g., $K_{prog}$ or $K_{pre}$) denotes the cell flux due to apoptosis. The factors of $2^{d_i}$ indicate amplification due to an average number of $d_{prog}$ or $d_{pre}$ rounds of cell division in the progenitor or precursor compartment, respectively. In other words, for Eq. (1.11), $$\frac{dn_{ery}}{dt}.$$

indicates a rate of change or the total amount of red blood cells, $2^{d_{pre}} J_{pre \to ery}$ indicates a differentiation flux from a precursors population to an erythrocytes population, $K_{ery}$ indicates cell fluxes due to apoptosis.

The total differentiation fluxes are given by the following equations.

$$J_{prog \to pre} = \omega_{prog \to pre} n_{prog}, \quad \text{Eq. (1.12)}$$

$$J_{pre \to ery} = \omega_{pre \to ery} v_{mat}(e) \phi_{iron} n_{pre}, \quad \text{Eq. (1.13)}$$

Here, $\omega_{i \to j}$ (e.g., $\omega_{pre \to ery}$ and $\omega_{prog \to pre}$) denotes the differentiation rate from population i to j, and $\phi_{iron}$ is a phenomenological parameter accounting for the availability of iron in plasma. Furthermore, $v_{mat}(e)$ denotes an epo-dependent regulation factor that leads to a de- or acceleration of maturation with changing EPO levels, which is described in the following equation.

$$v_{mat}(e) = \varphi_{a_{mat}, b_{mat}, q_{mat}, 1}(k_{mat}[e - e^*_{mat}]) \qquad \text{Eq. (1.14)}$$

where $e^*_{mat}$ at denotes EPO setpoint levels.

The cell death fluxes are given by the following equations.

$$K_{prog} = \kappa_{prog} \phi^- \left( \left[ \frac{e}{\bar{e}} \right]^{m_{prog}} \right) n_{prog}, \qquad \text{Eq. (1.15)}$$

$$K_{pre} = \omega_{pre \to ery}[1 - \phi_{iron}] n_{pre}, \qquad \text{Eq. (1.16)}$$

$$K_{ery} = k_{ery} n_{ery} + k_{neo}(e) n_{ery}, \qquad \text{Eq. (1.17)}$$

where $k_i$ (e.g., $k_{ery}$ and $\kappa_{prog}$) denote the apoptosis rates for cell population i and $\bar{e}$ is the Epo EC50 for downregulation of progenitor apoptosis, $k_{neo}$ denotes the rate of neocytolysis regulated by the hormone EPO given by:

$$k_{neo}(e) = \varphi_{a_{neo}, b_{neo}, q_{neo}}(k_{neo}[e - e_{neo}]), \qquad \text{Eq. (1.18)}$$

where $e_{neo}$ denotes the threshold for neocytolysis.

Note that the amount of available iron determines the relative fraction of precursor cells that are primed for apoptosis or differentiation, respectively; however, the overall 'loss' from the precursor cell compartment is independent of iron and given by $J_{pre \to ery} + K_{pre} = \omega_{pre \to ery} * n_{pre}$.

Regarding the hemoglobin and observables, since the variables $n_i$ denote the average progeny of a representative pool of BFU-Es (erythroid burst-forming unit), absolute cell population sizes are given by $Ni = Q_{prog} n_i$, where $Q_{prog} = 10^9$ is the conversion factor. Accordingly, the blood hemoglobin concentration is given by $$c_{hgb} = \lambda_{hgb} n_{ery} \qquad \text{Eq. (D)}$$

where $$\lambda_{hgb} = \frac{MCH}{V_{blood}} Q_{prog} \qquad \text{Eq. (1.23)}$$

In typical units, this reads:

$$\lambda_{hgb}[g/dl]^{-1} = 10^{-1} * \frac{MCH[pg]^{-1}}{V_{blood}[ml]^{-1}} \qquad \text{Eq. (1.24)}$$

The concentration of oxygenated hemoglobin in blood $\sigma_{O_2}$ is taken to depend on the blood hemoglobin concentration $c_{hgb}$ and O2 partial pressure $p_{O_2}$.

Figure 5B:
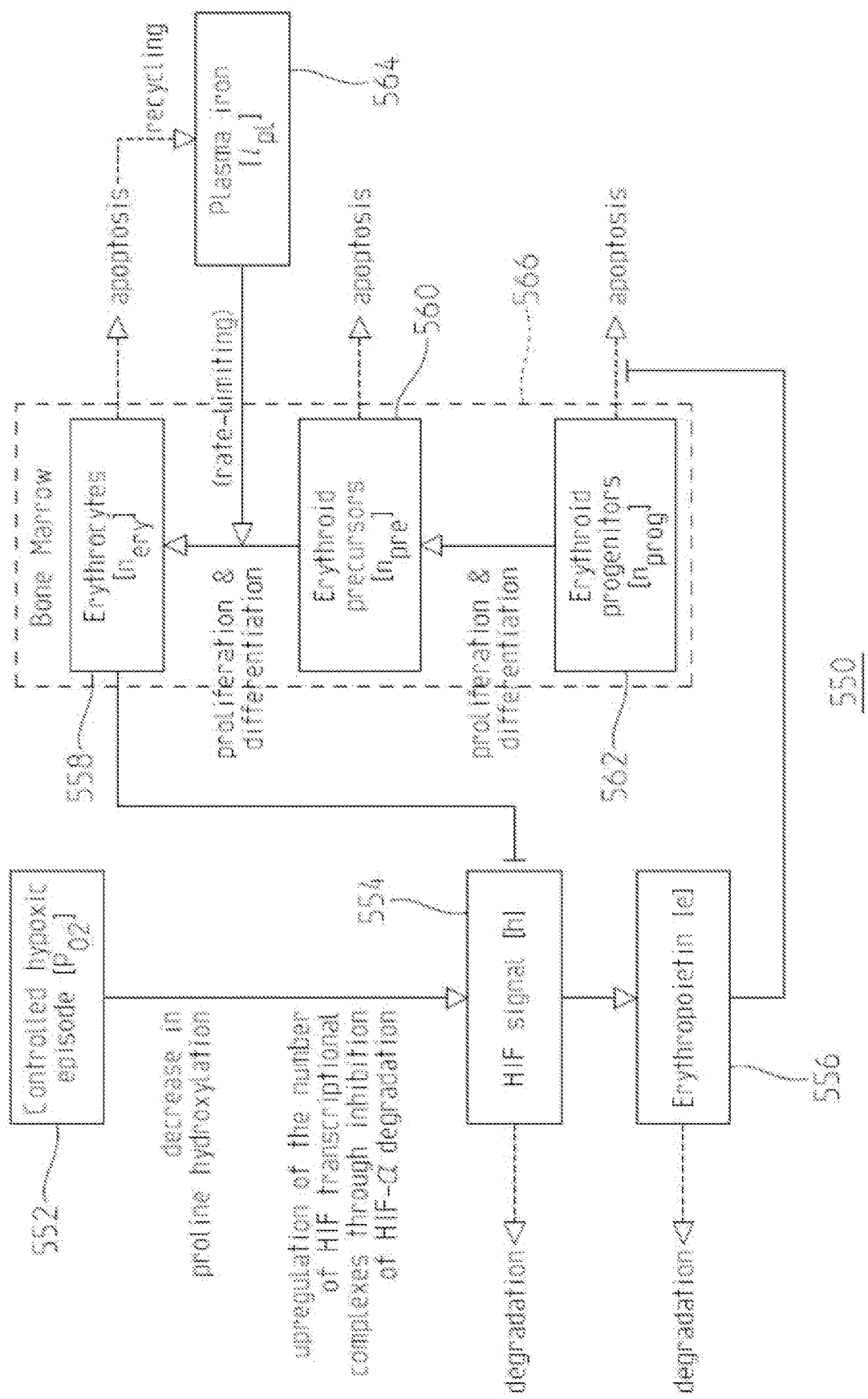
FIG. 5B is a block diagram describing blocks within the exemplary mathematical model of FIG. 5A according to one or more examples of the present application.

FIG. 5B is a block diagram describing blocks within the exemplary mathematical model of FIG. 5A according to one or more examples of the present application. For instance, FIG. 5B includes various physiological processes at work. For instance, FIG. 5B shows block 552 for the controlled hypoxic episode, block 554 for the HIF signal, block 556 for the erythropoietin, block 566 for the bone marrow that includes the erythrocytes block 558, the erythroid precursors 560, and the erythroid progenitors 562, and block 564 for the plasma iron. These blocks are described above in FIG. 5A.

Figure 6A:
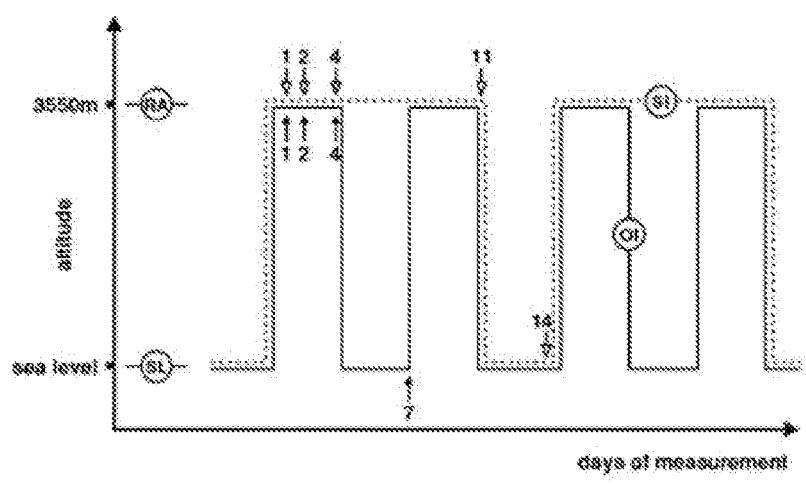
FIG. 6A is a figure from a prior study on Chilean soldiers showing the timetable of intermittent hypoxic exposure.

Now turning to FIG. 6A, there was a study in Chile that included subjecting members of the Chilean Army to intermittent hypoxic exposure at high altitude (3550 m). FIG. 6A shows the timetable of intermittent hypoxic exposure for the subject groups in this study. FIG. 6A is from a publication on the study, the publication is Heinicke K, Prommer N, Cajigal J, Viola T, Behn C, Schmidt W. Long-term exposure to intermittent hypoxia results in increased hemoalobin mass, reduced plasma volume, and elevated erythropoietin plasma levels in man. Eur J Appl Physiol. 2003 February; 88(6):535-43. doi: 10.1007/s00421-002-0732-z. Epub 2002 Dec. 14. PMID: 12560952s, which is incorporated herein by reference in its entirety. FIG. 6A shows soldiers and officers who were subjected to intermittent hypoxia (SI for the solider groups and OI for the officer groups, which are represented by dashed and solid lines respectively). The blood was sampled from SI subjects on days 1, 2, 4, 11, and 14 (empty arrows) and from OI subjects on days 1, 2, 4, and 7 (filled arrows). The SL soldiers are at sea level and the RA residents are at attitude. The SI group comprised ten soldiers who experienced several periods of intermittent hypoxia. They had served for 6 months alternating between 3,550 m at altitude (11-day periods) and sea level (3-day periods). The OI group comprised nine officers who experienced intermittent hypoxia. They had served for about 22 years alternating between 3,550 m altitude (3.5-day periods) and sea level (3.5-day periods).

Figure 6B:
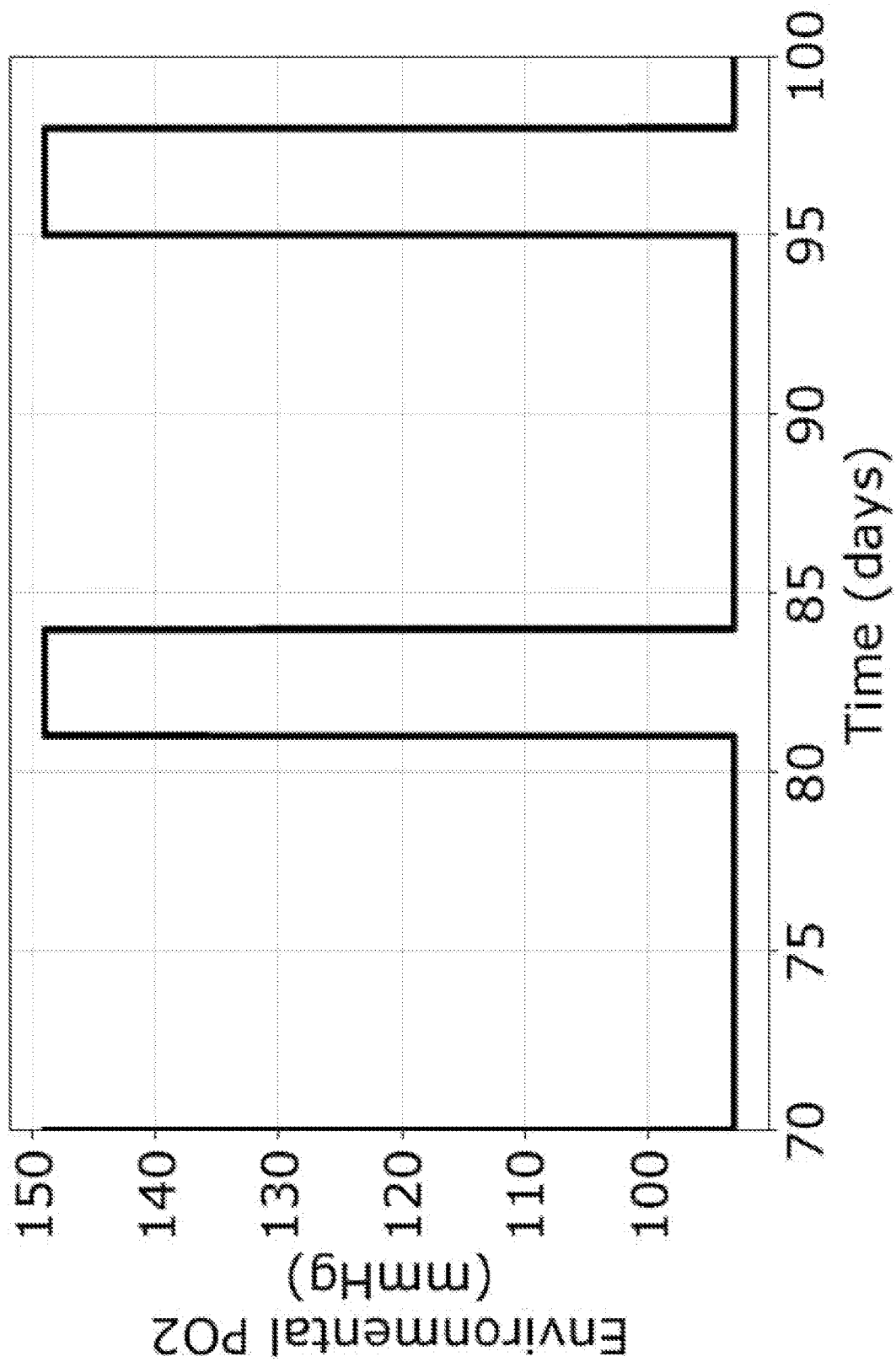
FIGS. 6B-6K show graphical representations of using the generated erythropoiesis models according to one or more examples of the present application.
Figure 6C:
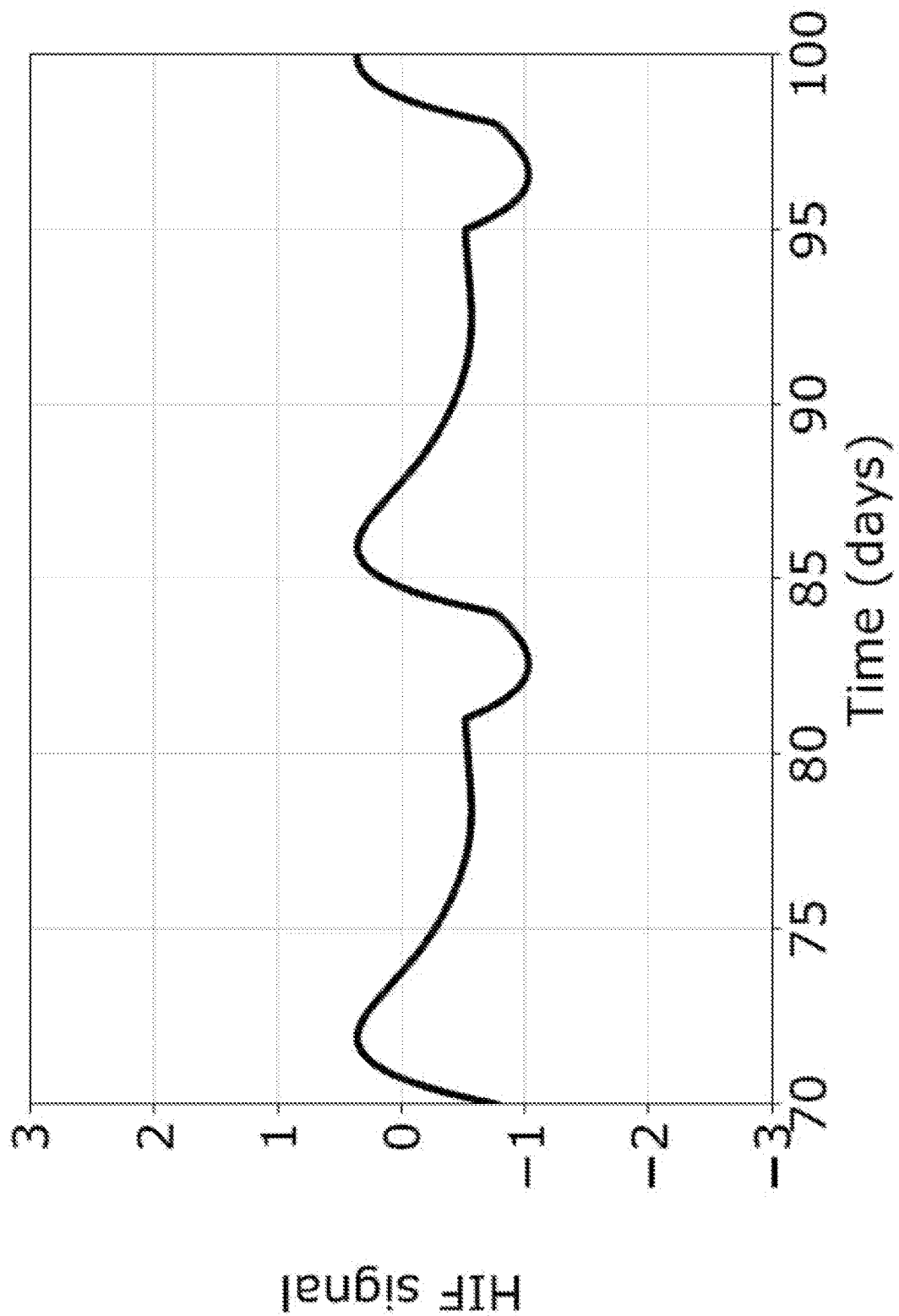
Figure 6D:
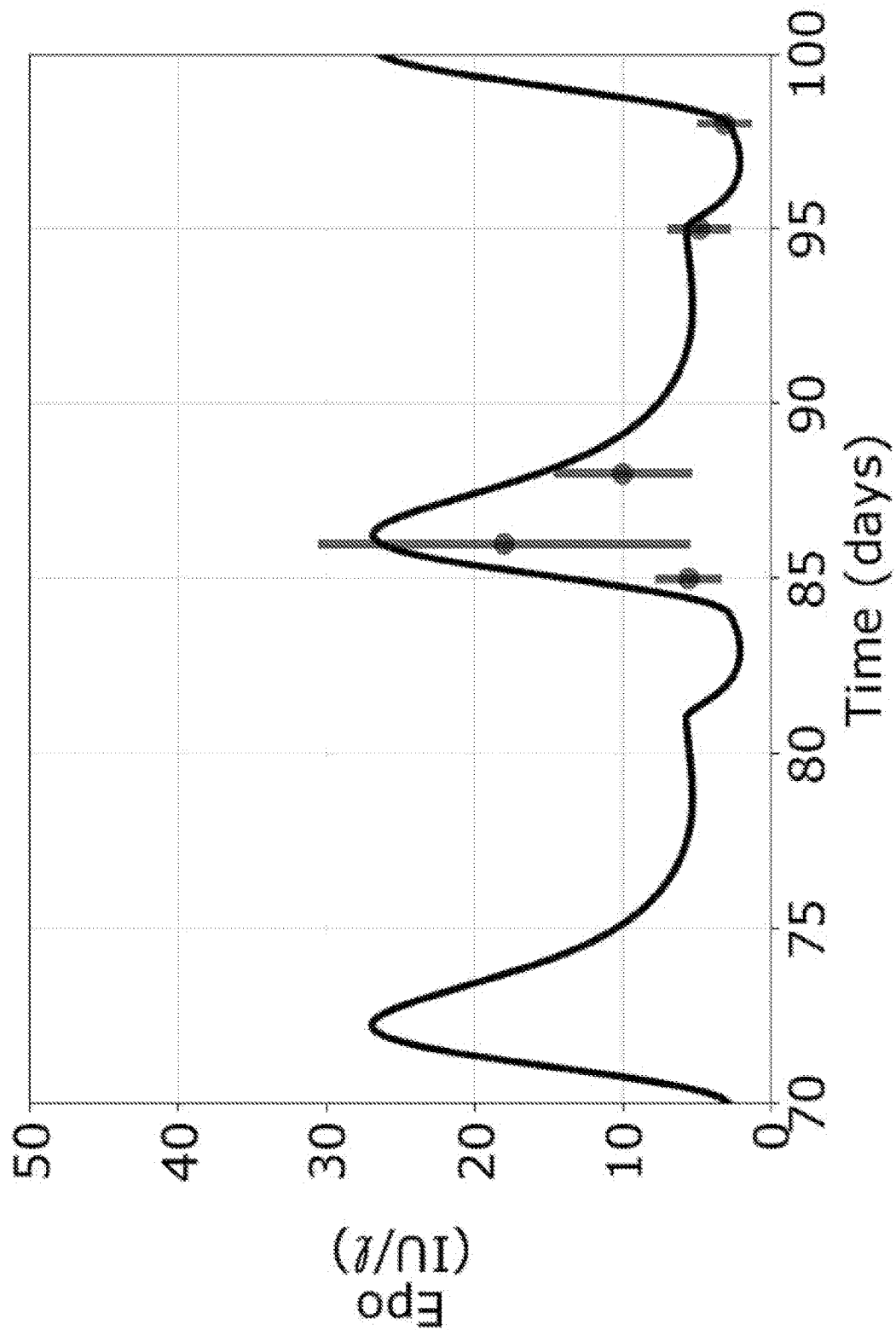
Figure 6E:
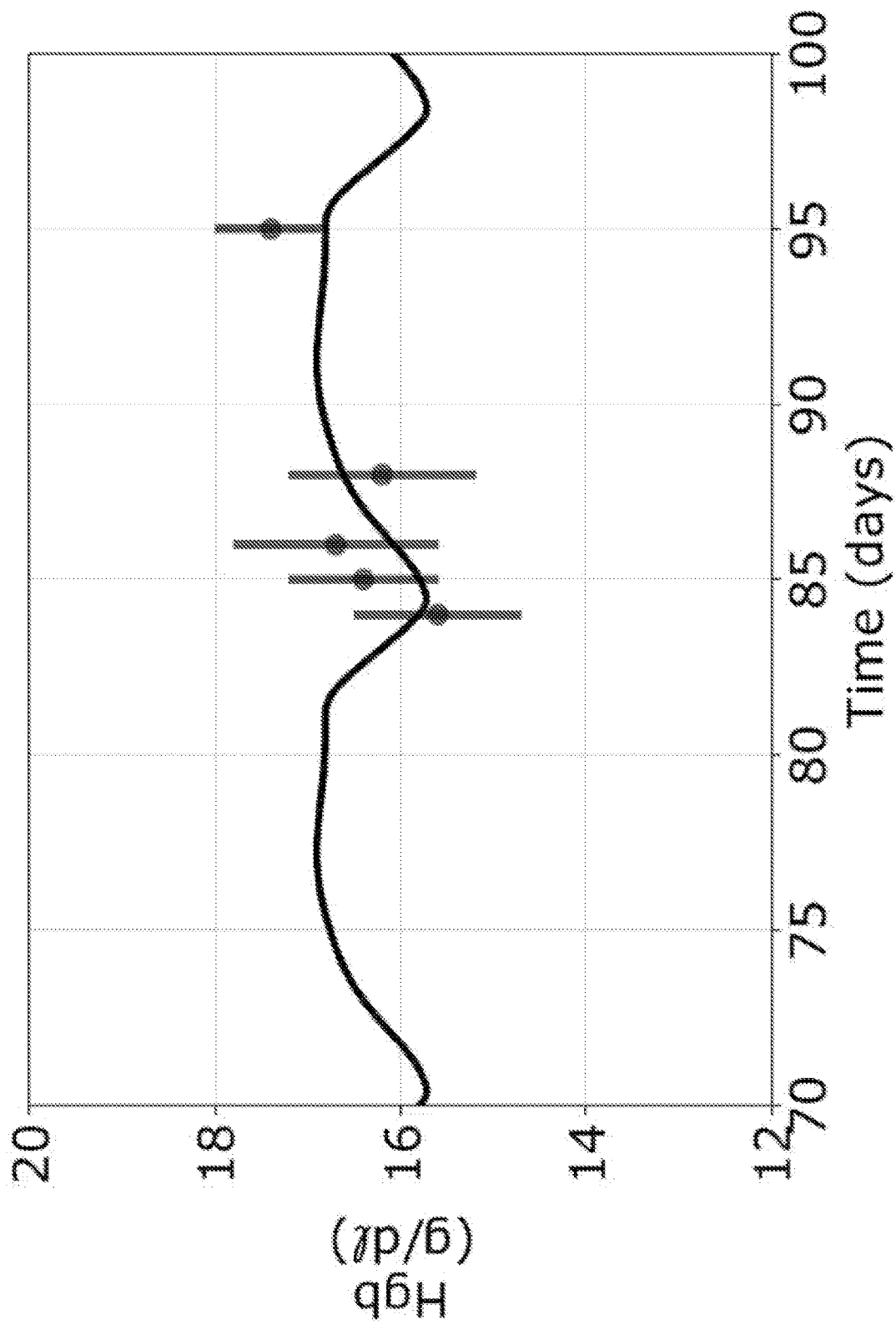
Figure 6F:
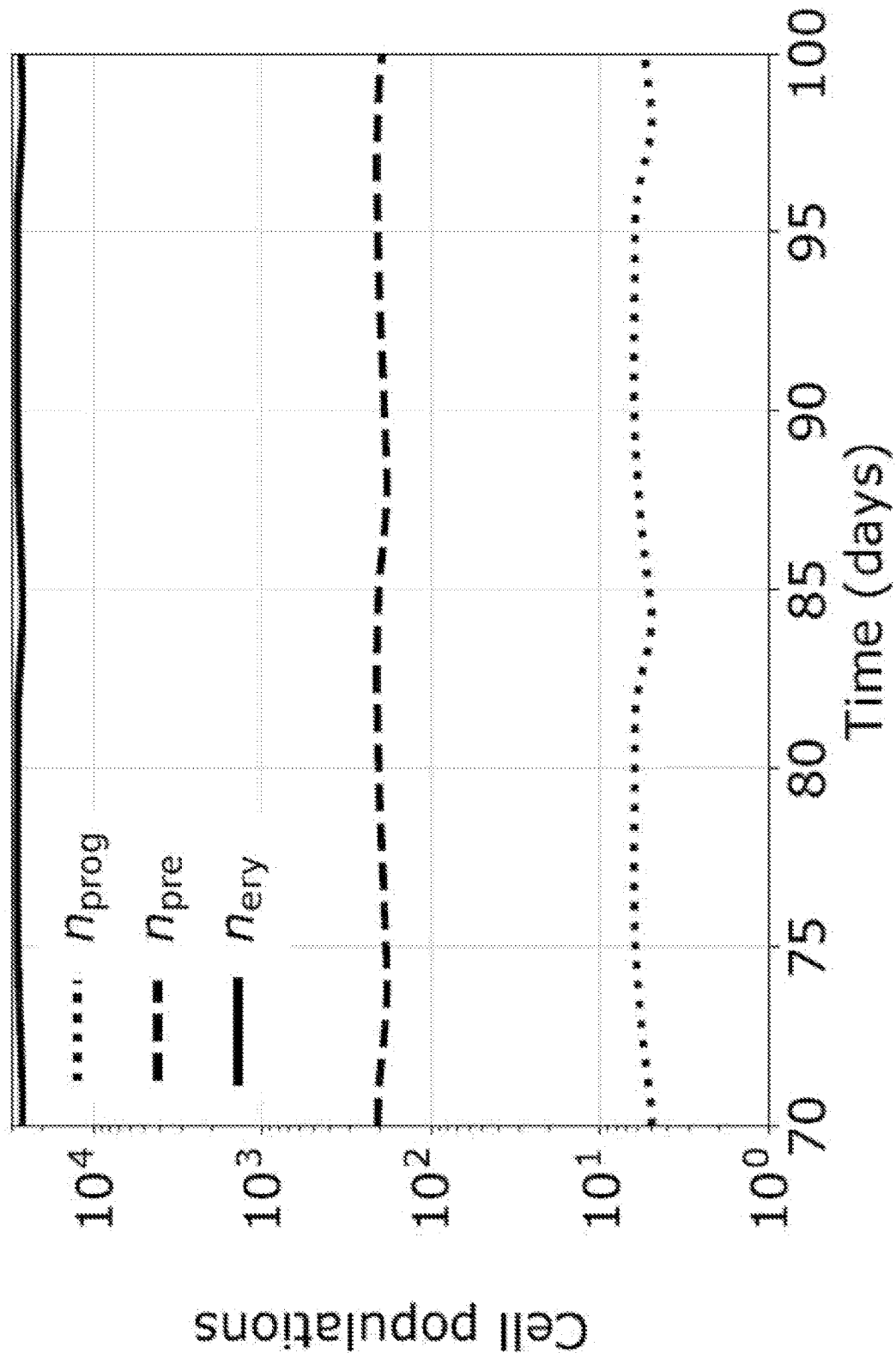

To validate the erythropoiesis model above, the experimental data from the Chilean study was input into the erythropoiesis model and the results from the model are shown in the FIGS. 6B-6K. FIGS. 6B-6F show graphical representations of using the above erythropoiesis model to the hypoxic exposure experienced by the soldiers of the study (e.g., SI from FIG. 6A). For instance, FIG. 6B shows the environmental PO2 (model variable $p_{O_2}$, Eq. 1.7) over a period of time. FIG. 6C shows the HIF signal (model variable h, Eq. 1.6) over a period of time. FIG. 6D shows the serum EPO concentration (model variable e, Eq. 1.8) over a period of time as well as shows the actual measured serum EPO concentration (e.g., the dots with the vertical lines, with the dots indicating the mean and the vertical lines indicating the standard deviation). FIG. 6E shows the blood hemoglobin concentration (model variable $c_{hgb}$, Eq. 1.7) over a period of time as well as shows the actual measured HGB data points (e.g., the dots with the vertical lines, with the dots indicating the mean and the vertical lines indicating the standard deviation). FIG. 6F shows the abundance of cell populations (model variables $n_{prog}$, $n_{pre}$, $n_{ery}$, Eqs. 1.9-1.11) over a period of time.

Figure 6G:
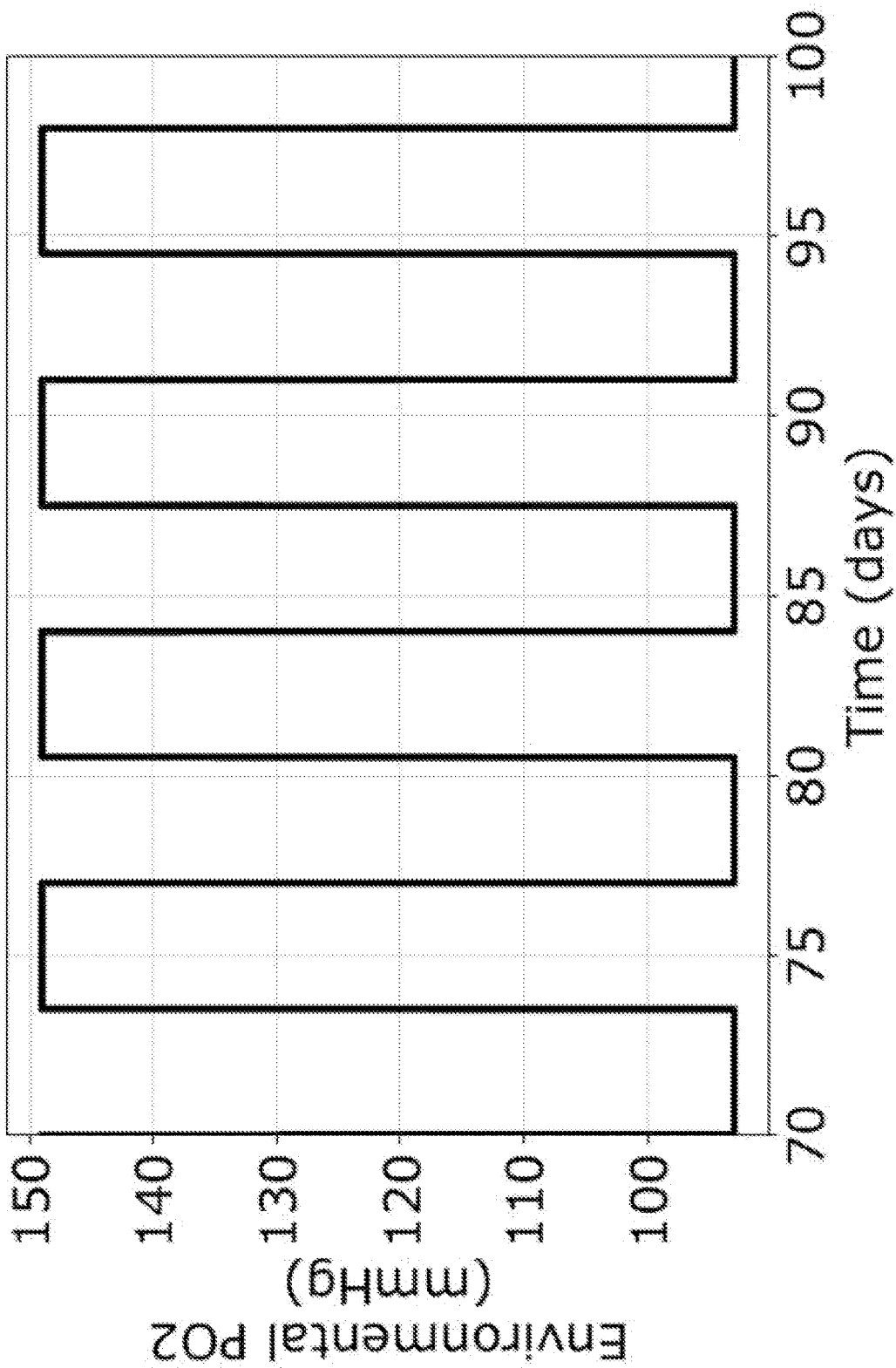
Figure 6H:
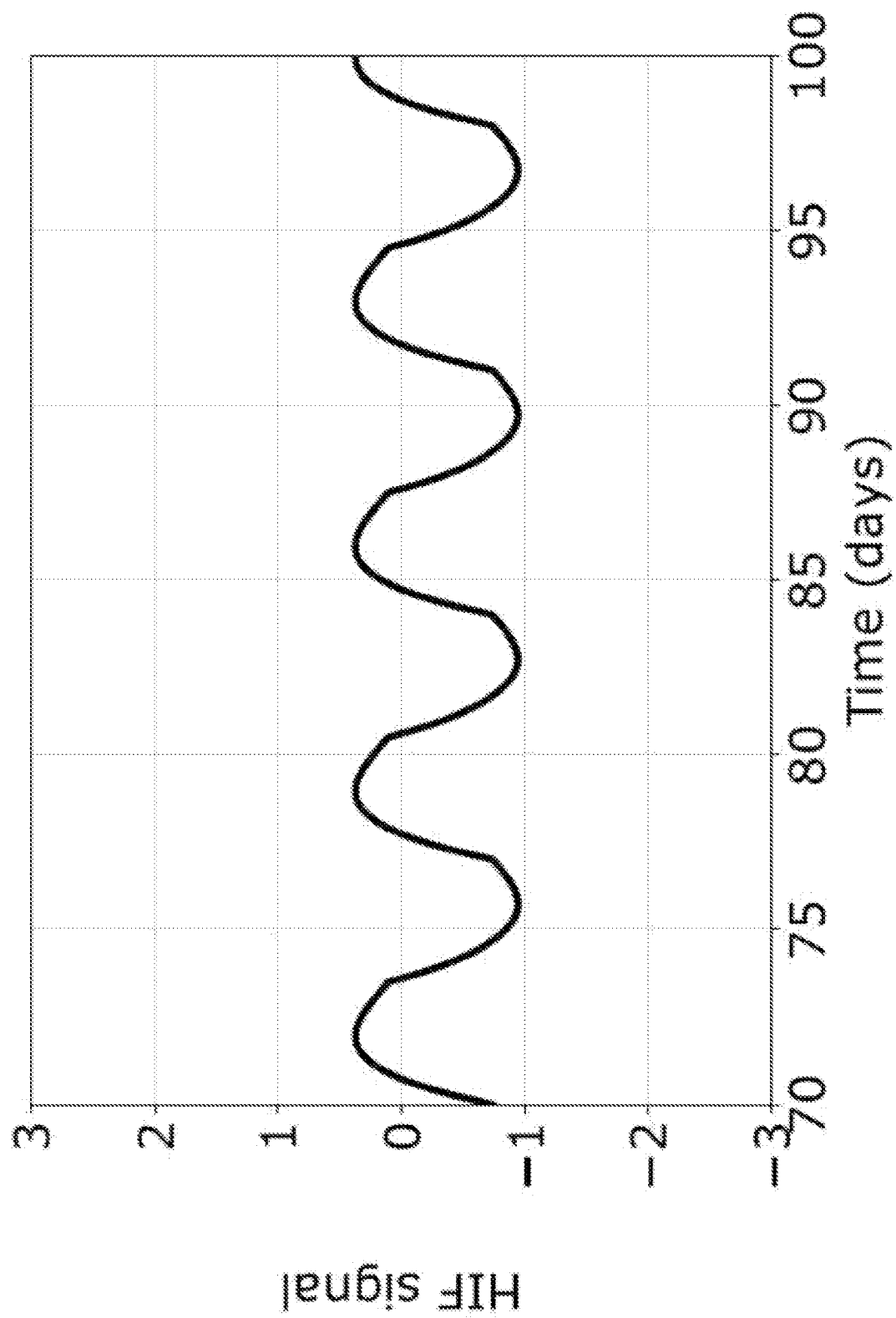
Figure 6I:
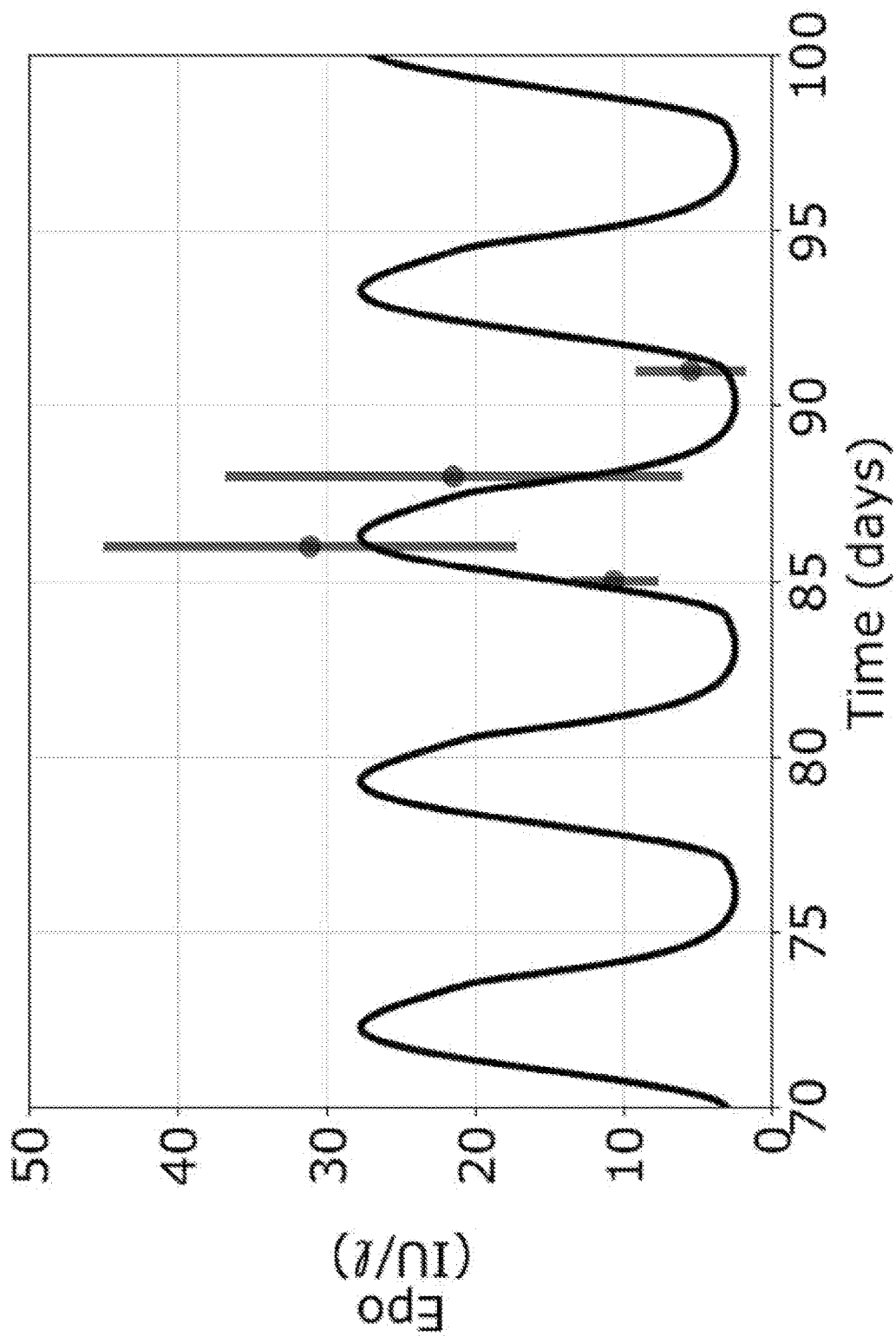
Figure 6J:
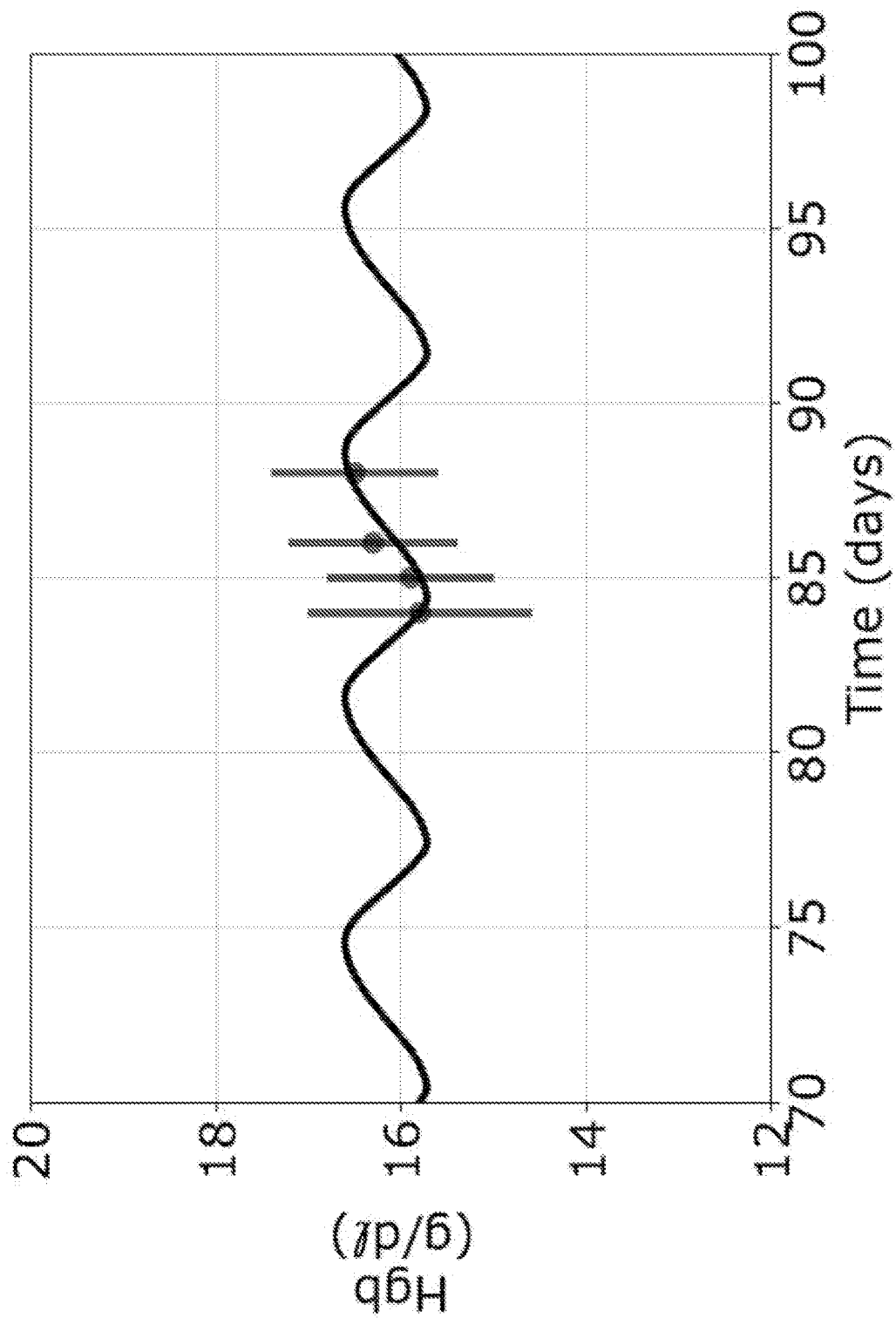
Figure 6K:
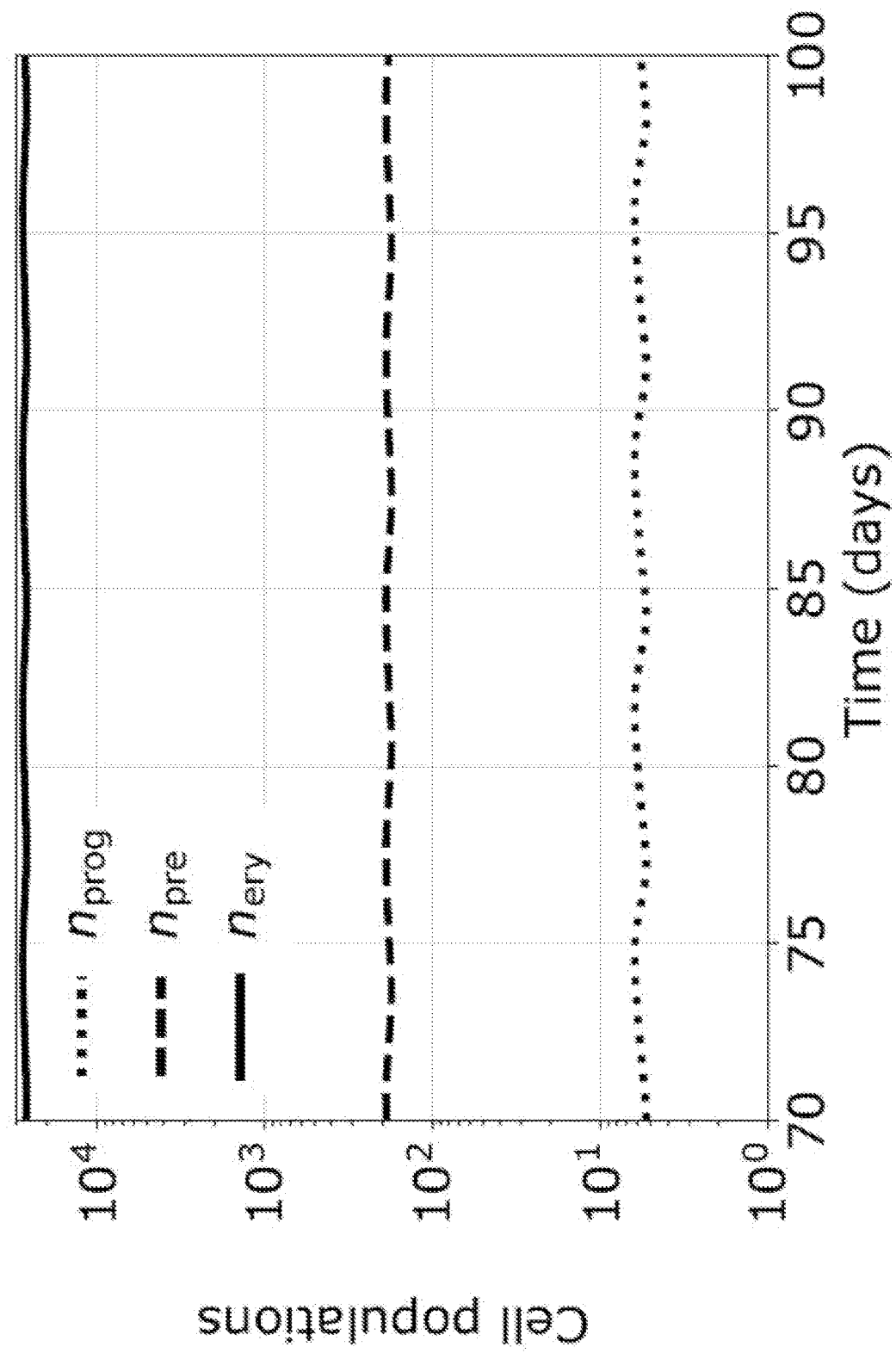

FIGS. 6G-6K show graphical representations of using the above erythropoiesis model to the hypoxic exposure experienced by the officers of the study (e.g., OI from FIG. 6A). For instance, FIG. 6G shows the environmental PO2 (model variable $p_{O_2}$, Eq. 1.7) over a period of time. FIG. 6H shows the HIF signal (model variable h, Eq. 1.6) over a period of time. FIG. 6I shows the serum EPO concentration (model variable e, Eq. 1.8) over a period of time as well as shows the actual measured serum EPO concentration (e.g., the dots with the vertical lines, with the dots indicating the mean and the vertical lines indicating the standard deviation). FIG. 6J shows the blood hemoglobin concentration (model variable $c_{hgb}$, Eq. 1.7) over a period of time as well as shows the actual measured HGB data points (e.g., the dots with the vertical lines, with the dots indicating the mean and the vertical lines indicating the standard deviation). FIG. 6K shows the abundance of cell populations (model variables $n_{prog}$, $n_{pre}$, $n_{ery}$, Eqs. 1.9-1.11) over a period of time.

It will be appreciated that the various machine-implemented operations described herein may occur via the execution, by one or more respective processors, of processor-executable instructions stored on a tangible, non-transitory computer-readable medium, such as a random access memory (RAM), read-only memory (ROM), programmable read-only memory (PROM), and/or another electronic memory mechanism. Thus, for example, operations performed by any device described herein may be carried out according to instructions stored on and/or applications installed on the device, and via software and/or hardware of the device.

All references, including publications, patent applications, and patents, cited herein are hereby incorporated by reference to the same extent as if each reference were individually and specifically indicated to be incorporated by reference and were set forth in its entirety herein.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present application covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A computing system, comprising:
    a user device, comprising:
        one or more sensors configured to obtain partial pressure of oxygen (PO2) levels;
        one or more first processors; and
        a first non-transitory computer-readable medium having first processor-executable instructions stored thereon, wherein the first processor-executable instructions, when executed by the one or more first processors, facilitate:
            obtaining, using the one or more sensors, the PO2 levels over a period of time;
            generating previous PO2 information for a user based on the PO2 levels obtained using the one or more sensors; and
            providing the previous PO2 information to a personalized erythropoiesis model generation computing platform; and
    the personalized erythropoiesis model generation computing platform, comprising:
        one or more second processors; and
        a second non-transitory computer-readable medium having second processor-executable instructions stored thereon, wherein the second processor-executable instructions, when executed by the one or more second processors, facilitate:
            obtaining the previous PO2 information from the user device;
            obtaining individualized user data for the user, wherein the individualized user data indicates one or more previous hematocrit and/or hemoglobin measurements for the user;
            determining an individualized erythropoiesis model for the user based on the one or more previous hematocrit and/or hemoglobin measurements and the previous PO2 information, wherein the individualized erythropoiesis model indicates a set of individualized model parameters for the user;
            employing the individualized erythropoiesis model to determine one or more predicted hematocrit and/or hemoglobin measurements at one or more future instances in time; and
            performing one or more actions based on the one or more predicted hematocrit and/or hemoglobin measurements.

2. The computing system of claim 1, wherein determining the individualized erythropoiesis model for the user comprises:
    inputting the previous PO2 information and the one or more previous hematocrit and/or hemoglobin measurements into a mathematical model for oxygen dosing to determine the individualized erythropoiesis model.

3. The computing system of claim 1, wherein the previous PO2 information indicates one or more low oxygen events experienced by the user over a previous time period, wherein each of the one or more low oxygen events indicates a PO2 level that is below a normoxia level.

4. The computing system of claim 1, wherein employing the individualized erythropoiesis model to determine the one or more predicted hematocrit and/or hemoglobin measurements comprises:
    generating a plurality of future PO2 information, wherein each of the plurality of future PO2 information indicates one or more low oxygen events for the user to perform in a future time period;
    inputting the plurality of future PO2 information into the individualized erythropoiesis model to determine a plurality of predicted hematocrit and/or hemoglobin measurements; and
    determining an optimal future PO2 information from the plurality of future PO2 information based on comparing the plurality of predicted hematocrit and/or hemoglobin measurements with a desired hematocrit and/or hemoglobin measurement associated with the user.

5. The computing system of claim 4, wherein the second processor-executable instructions, when executed by the one or more second processors, further facilitate:

determining a systematic training strategy for the user based on the optimal future PO2 information, and wherein performing the one or more actions comprises displaying the systematic training strategy on a display device associated with the personalized erythropoiesis model generation computing platform.

6. The computing system of claim 1, wherein the first processor-executable instructions, when executed by the one or more first processors, further facilitate:

generating additional PO2 information for the user based on the PO2 levels obtained using the one or more sensors; and providing the additional PO2 information to the personalized erythropoiesis model generation computing platform.

7. The computing system of claim 6, wherein the second processor-executable instructions, when executed by the one or more second processors, further facilitate:

subsequent to employing the individualized erythropoiesis model, determining whether to re-employ the individualized erythropoiesis model; and re-employing the individualized erythropoiesis model using the additional PO2 information from the user device.

8. The computing system of claim 1, wherein the first processor-executable instructions, when executed by the one or more first processors, further facilitate:

obtaining a mathematical model for oxygen dosing;

obtaining population user data associated with a plurality of users; and generating a plurality of virtual user avatars based on the mathematical model and the population user data, wherein determining the individualized erythropoiesis model for the user is further based on the plurality of virtual user avatars.

9. The computing system of claim 1, wherein determining the individualized erythropoiesis model for the user is based on the following equation:

$$\frac{dh}{dt} = \beta_h(\theta)\varphi_{a_h,b_h,q_{h,0}}(k_h[\sigma_{O_2} - \sigma^*_{O_2}]) - k_h h$$

where $\frac{dh}{dt}$ indicates a rate of change of hypoxia-inducible factor (HIF) signaling activity, $\beta_h(\theta)$ indicates a formation rate of HIF complexes, $\varphi_{a_h,b_h,q_{h,0}}$ indicates a hypoxic upregulation of a HIF signal in response to decreases in blood hemoglobin concentration, $k_h$ indicates a decay rate of the HIF signal, $\sigma_{O_2}$ indicates a concentration of oxygenated hemoglobin in blood measured by kidneys, $\sigma^*_{O_2}$ indicates a physiological set point for the concentration of oxygenated hemoglobin in blood, and h indicates the HIF signal.

10. The computing system of claim 1, wherein determining the individualized erythropoiesis model for the user is based on the following equation:

$$\frac{de}{dt} = \beta_e(\theta) + \beta_e(\theta)\varphi_{a_e,b_e,q_{e,0}}(k_e h) - k_e e$$

where $\frac{de}{dt}$ indicates a EPO concentration rate of change, $\beta_e(\theta)$ indicates basal erythropoietin (EPO) synthesis under steady-state conditions, $\beta_e(\theta)(\varphi_{a_e,b_e,q_{e,0}}(k_e h))$ indicates additional EPO synthesis due to activation by a HIF signal, and $k_e e$ indicates EPO decay with a decay rate $k_e$.

11. The computing system of claim 1, wherein determining the individualized erythropoiesis model for the user is based on the following equation:

$$\frac{dn_{ery}}{dt} = 2^{d_{pre}} J_{pre \to ery} - K_{ery}$$

where $\frac{dn_{ery}}{dt}$ indicates a rate of change of the total amount of red blood cells, $2^{d_{pre}} J_{pre \to ery}$ indicates a differentiation flux from a precursors population to an erythrocytes population, and $K_{ery}$ indicates cell fluxes due to apoptosis.

12. A method, comprising:

obtaining individualized user data for a user, wherein the individualized user data indicates one or more previous hematocrit and/or hemoglobin measurements for the user and previous partial pressure of oxygen (PO2) information for the user;

determining an individualized erythropoiesis model for the user based on the one or more previous hematocrit and/or hemoglobin measurements and the previous PO2 information, wherein the individualized erythropoiesis model indicates a set of individualized model parameters for the user;

employing the individualized erythropoiesis model to determine one or more predicted hematocrit and/or hemoglobin measurements at one or more future instances in time; and performing one or more actions based on the one or more predicted hematocrit and/or hemoglobin measurements.

13. The method of claim 12, wherein determining the individualized erythropoiesis model for the user comprises:

inputting the previous PO2 information and the one or more previous hematocrit and/or hemoglobin measurements into a mathematical model for oxygen dosing to determine the individualized erythropoiesis model.

14. The method of claim 12, wherein the previous PO2 information indicates one or more low oxygen events experienced by the user over a previous time period, wherein each of the one or more low oxygen events indicates a PO2 level that is below a normoxia level.

15. The method of claim 12, wherein employing the individualized erythropoiesis model to determine the one or more predicted hematocrit and/or hemoglobin measurements comprises:

generating a plurality of future PO2 information, wherein each of the plurality of future PO2 information indicates one or more low oxygen events for the user to perform in a future time period;

inputting the plurality of future PO2 information into the individualized erythropoiesis model to determine a plurality of predicted hematocrit and/or hemoglobin measurements; and determining an optimal future PO2 information from the plurality of future PO2 information based on comparing the plurality of predicted hematocrit and/or hemoglobin measurements with a desired hematocrit and/or hemoglobin measurement associated with the user.

16. The method of claim 15, further comprising:
    determining a systematic training strategy for the user based on the optimal future PO2 information, and
    wherein performing the one or more actions comprises displaying the systematic training strategy on a display device associated with the personalized erythropoiesis model generation computing platform.

17. The method of claim 12, wherein determining the individualized erythropoiesis model for the user is based on the following equation:

$$\frac{dh}{dt} = \beta_h(\theta)\varphi_{a_h,b_h,q_{h,0}}(k_h[\sigma_{O_2} - \sigma^*_{O_2}]) - k_h h$$

where $\frac{dh}{dt}$ indicates a rate of change of hypoxia-inducible factor (HIF) signaling activity, $\beta_h(\theta)$ indicates a formation rate of HIF complexes, $\varphi_{a_h,b_h,q_{h,0}}$ indicates a hypoxic upregulation of a HIF signal in response to decreases in blood hemoglobin concentration, $k_h$ indicates a decay rate of the HIF signal, $\sigma_{O_2}$ indicates a concentration of oxygenated hemoglobin in blood measured by kidneys, $\sigma_{O_2}^*$ indicates a physiological set point for the concentration of oxygenated hemoglobin in blood, and h indicates the HIF signal.

18. The method of claim 12, wherein determining the individualized erythropoiesis model for the user is based on the following equation:

$$\frac{de}{dt} = \beta_e(\theta) + \beta_e(\theta)\varphi_{a_e,b_e,q_{e,0}}(k_e h) - k_e e$$

where $\frac{de}{dt}$ indicates a EPO concentration rate of change, $\beta_e(\theta)$ indicates basal erythropoietin (EPO) synthesis under steady-state conditions, $\beta_e(\theta)\varphi_{a_e,b_e,q_{e,0}}(k_e h)$ indicates additional EPO synthesis due to activation by a HIF signal, and $k_e e$ indicates EPO decay with a decay rate $k_e$.

19. The method of claim 12, wherein determining the individualized erythropoiesis model for the user is based on the following equation:

$$\frac{dn_{ery}}{dt} = 2^{d_{pre}} J_{pre \to ery} - K_{ery}$$

where $\frac{dn_{ery}}{dt}$ indicates a rate of change of the total amount of red blood cells, $2^{d_{pre}} J_{pre \to ery}$ indicates a differentiation flux from a precursors population to an erythrocytes population, and $K_{ery}$ indicates cell fluxes due to apoptosis.

20. A personalized erythropoiesis model generation computing platform, comprising:
    one or more processors; and
    a non-transitory computer-readable medium having processor-executable instructions stored thereon, wherein the processor-executable instructions, when executed by the one or more processors, facilitate:
        obtaining individualized user data for a user, wherein the individualized user data indicates one or more previous hematocrit and/or hemoglobin measurements for the user and previous partial pressure of oxygen (PO2) information for the user;
        determining an individualized erythropoiesis model for the user based on the one or more previous hematocrit and/or hemoglobin measurements and the previous PO2 information, wherein the individualized erythropoiesis model indicates a set of individualized model parameters for the user;
        employing the individualized erythropoiesis model to determine one or more predicted hematocrit and/or hemoglobin measurements at one or more future instances in time; and
        performing one or more actions based on the one or more predicted hematocrit and/or hemoglobin measurements.

* * * * *